(12) United States Patent
Rubin et al.

(10) Patent No.: US 6,509,457 B1
(45) Date of Patent: Jan. 21, 2003

(54) COMPOSITIONS AND METHODS FOR MODULATING APOPTOSIS

(75) Inventors: Raphael Rubin, Penn Valley; Manorama Tewari, East Lansdowne, both of PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/234,245

(22) Filed: Jan. 20, 1999

Related U.S. Application Data

(60) Provisional application No. 60/071,878, filed on Jan. 20, 1998.

(51) Int. Cl.[7] .......................... C07H 21/04; C07H 5/04; C07H 5/06; C07H 19/00; C07H 21/00
(52) U.S. Cl. ..................... 536/23.5; 536/1; 536/18.7; 536/22.1; 536/23.1; 536/23.4; 435/320.1; 435/325; 435/41; 435/69.1; 530/350
(58) Field of Search ..................... 536/1, 18.7, 22.1, 536/23.1, 23.4, 23.5; 435/320.1, 325, 41, 69.1; 530/350

(56) References Cited

PUBLICATIONS

Tewari et al. AAC–11, a Novel cDNA that inhibits apoptosis after Growth Factor Withdrawal. Cancer Research 57:4063–4069, 1997.*

Amino acid databases, Accession Nos. O15441, O35841, U35846 and U83857, 1997 & 1998.*

Nucleic acid databases, Accession Nos. O15441, O35841, U35846, U83857, 1997 & 1998.*

* cited by examiner

*Primary Examiner*—Sheela Huff
*Assistant Examiner*—Alana M. Harris
(74) *Attorney, Agent, or Firm*—Dechert; Thomas S. Deibert

(57) ABSTRACT

AAC-11 polypeptide and DNA (RNA) encoding AAC-11 polypeptide and methods for producing such polypeptide by recombinant techniques. Also, methods of using the AAC-11 polynucleotides and/or polypeptides to inhibit apoptosis in cells. Further, methods of using agonists or antagonists to AAC-11 polypeptides to inhibit or induce apoptosis in cells.

15 Claims, 12 Drawing Sheets

FIG. 1A

```
ttggctctccagggtaaatcaggcgaggcctaaaacagaggagaacagataaagttgttgcactgaaataacaacaatatcaat  1350
 L  A  L  Q  G  K  T  G  E  A  L  K  T  E  E  N  K  I  K  V  V  A  L  K  I  T  N  N  I  N
gttttaatcaaggatctcttccacattcctctccttcttataagagcacagtaacattgtcctgaaacctgtgcagaaagttgagattggg  1440
 V  L  I  K  D  L  F  H  I  P  P  S  Y  K  S  T  V  T  L  S  W  K  P  V  Q  K  V  E  I  G
caaaagagaaccagtgaagatacaagttcagttcaccacctaagaagtctccaggaggaccaaaagagatgccagacagattataat  1530
 Q  K  R  T  S  E  D  T  S  S  G  S  P  P  K  K  S  P  G  G  P  K  R  D  A  R  Q  I  Y  N
              A  +                          T                                S  A
cctccgagtggaaagtacagcagcaatctgagcaactttaattatgaggagccttcaggggaaatagaggtggccgaggttgggaac  1620
 P  P  S  G  K  Y  S  S  N  L  S  N  F  N  Y  E  R  S  L  Q  G  K  *
 L
acgagaaatcgaagtcgaggaagactctactgattgtgacgtcacattcttcagcattgtcatgagattaatatactaaatctactac  1710
tcattgattgccgggatgtcccttaaaagactgctgccttcagctgaaaatgtaatgttctttctaccttgtatgtatgatctac
ttttgtaaaagaccatgttgtgtccaagtgtaaaaccacacaacatattttggatgctgtctgcagccttgactgtttcacaatat  1890
cctcactatccagacttcatctgtgaatctccttgcttttcacacatctcttgatggttttcactgagatctgactctattggaaaagtcagtc  2070
tagcctgtgatctggtgaagatcatcactcttgaaacgttactgttctctcccaccatccgttaggtttctgccaacacatggagaaga
gttaagagcagtcttaacctctgctttcattgtttctcaaggaagctgctaggcagtgttgtcgcattcctgccaagtcatagaatga
agcaccagctctctcacagtgtacagggtcttattatttgaataggagtgtgcataatatacgtacagacataagcatatgtgtgtgtata  2250
atacagctttgaacacttgagtgtgacaacaatcaataataatctcggaagggtccctgacatagcgattatccctttgaggctgaat
tatgcatggaacttggctgtatctaggtttttcactcagtagtaggagggaatttcagtgaatacagccaacctacagttattattgttgtttaaaacta  2430
ccattactgactggtgttttacagagacaaatttaaagaacccttgttgtgaaatacagccagatctggtgtacatacaggttcccacagg
aaaaacaaaggctgttttaaggattggagactttcaaatttaacttctcagttattaatcagattacttgtgtaagttagccaatagtcttag  2610
atctgctatgtaatgtcgctgcttttgccacttcaagtctctattcaggtgtctcatgttgcggcagttgtgggcagtctcatttgaagctcttcacac
gctcactccgctgcttttgcccacttcaaatttcactattcaagtcaagtgacaaatcagatgtgacattctacagttctagtggttttgtttatg  2790
attaaggcaacagacgggaggtcgtggagtcagttttcattctttactacacaggtgttttcatcaccatcaatttacactggggaaaaacaattcctttgtgag
attttgtcacagttcaatcttccagagttttcattttgaaaatattttgaaagttagtggagctggtatagaaagttgatacaagtggagcttgcagcttgcagcttgcatggagtg  2970
aatcactgcaagtatttatgcgaacattcgacaccagcctgagctgaacctagctcagccatgcagcgatatcagcgatcatgccatcaagccaactttcaagcttgtaaactcggcagaagtaactaactttaaaatgaattgactatagc
ctggcaataaacttgaacatttgaacattgaagctgagctgagaagatcagcagcatgcagcatgtacatatgaatgccgatgcagtgccagcatggactatgc  3150
tgaatcctgtgaccatttagttatgaccctcagagatgtgcctgaaggcatttgtcctgtgaaactcggcagaagtaactgacctcatgtcactgcaga
aacataaatttgaacacagtaacttttctctttgctcctcctccccctcgcaaggacacctgtctccccttgttaaataaatgtaaatgctccctatg  3330
gctcactgcattcacccctcctcatcttttcttctccgcaaggacacctgtctccccttgttaaataaatgtaaatgctccctatg  3510
ctgaaagaaaatcttcatgccatcaatctttcttgtaaaaaaaaaaaaaaaaaaaaaaaaaaaaaaaaaaaaaaa
ctttgaaattttcctttgtaaaaaaaaaaaaaaaaaaaaaaaaaaaaaaaaaaaaaaaaaaaaaa  3690
aaaaaaaaaaaaaaaaaaaa 3714
```

FIG. 1B

Figure 6a (A) *Mus musculus* AAC-11$_{long}$ polynucleotide sequence [SEQ ID NO:1].

5'-ATTCCTCAGATAAGTTCCGTGGAGGCGGGCGGTGGGCGAACTGGCGCTCAGCATGCCGACGGTGGAG
GAGCTGTACCGCAACTACGGCATCCTCGCCGATGCCAGCCACGGAGCAAGTGGGCCAGCATAAAGATGCCTACCAAGTGATACTGGCGTGAAAGGCGGCACCA
AGGAAAAGCGATTAGCAGCTCAGTTTATACCAAAATTCTTAAGCATTTTCCAGAGCTGGCTGATTCTGCTATCAATGCACAGTTAGACCTCTGTGAGGATGA
AGATGTGTCAATACGACGTCAAGCAGTCAAGCAATTAAAGAGCTGCCTCAGTTTGCCACAGAGAGAAACCTTCCTAGAGTAGCAGATATACTGACCCAGCTTCTGCAGACA
GATGACTCTGCAGAATTAACCTGGTGAACAATGCTCTGCTAAGTATATTTAAGATGGATGCAAAAGGAACGTTAGGTGGCTTGTTGTTTAGCCAGATTCTTCAAG
GAGAAGACATTGTTAGAGAACGAGCAGCAATTAAATTCCTGTCCACAAAACTCAAGACGCTCCCAGATGAGGTGTTGACTAAGGAAGTGGAGGAACTCATACTCAC
TGAGTCCAAGAAGTCCTAGAGAGACGTGACTGGTGAAGAGTTTGTTTTGTTCATGAAGATACTGTCTGGGTTGAAAAGCTTACAGACAGTGAGTGGACGACAG
CAGCTGGTGAGCTGGTGGCGCAGAACAGGCTGACCTGGGGAACAGGCGGCCTTCAGCCTCTATTTCTGTGACGTATTTGTGACCAGTTCTCCCTAACCTCAGACCACCCAGTGAAGCCT
TGCCTCTTCTCCAAAAATGTGCATTCTACAAGATTTGTTTGGGCAGAGATGAGTTCATTTTGTGGTGTAATGAGGAGAATGCTGGTAATGCAAGTCGAGTTCGTCAGTGGCCCAAGCTGCAGTTCAGTTATGTGGAGTGCTTATTGTACA
CGATATACAGCTGGAGTTATGCCTCTCCCTCCAGAGAAGCAGAACAGGATTCTTAACAGCCAAACTGATGAGGAACCTGAAAAACTCAAGGATTTCAAAATTAGGTTGCAGTACTTTGCACGGGG
TTGGAGTATATGCCTCTCCCTCCAGAGAAGCAGAACAGGATTCTTAACAGCCAAACTGATGAGGAACCTGAAAAACTCAAGGATTTCAAAATTAGGTTGCAGTACTTTGCACGGGG
GTTTTCATCAGTTTATATCGAGATGTTTAATCAAGGATCTCTTCCAGACTTCGCTTGGCTCTCCAGGGTAAAACAGGCGAGGCTTAAAAACAGAGAACATTGTCCTGGAAACCTGTGCAGAAAGTTGAGATTG
CCTGCAGGTTTATATCGAGATGTTTAATCAAGGATCTCTTCCAGACTTCGCTTGGCTCTCCAGGGTAAAACAGGCGAGGCTTAAAAACAGAGAACATTGTCCTGGAAACCTGTGCAGAAAGTTGAGATTG
ACAAACAATATCAATGTTTAATCAAGATACAAGTTCAGGTTCAAGTTCAGGTTCACCAATTCCTCCACCACCTAAGAAGTCTCCAGGGGAAATAGAGGTGGGCCGAGGTTGGGGAACACGGAGATCGAGGAAG
GGCAAAAGAGAACCAGTGAAGATACAAGTTCAGGTTCAAGTTCAATTGAGAGGCCTTCAGGGGAAATAGAGGTGGGCCGAGGTTGGGGAACACGAGATTATAATCCTCCGAGTGG
AAAGTACAGCAGCAATCTGAGCAACTTTAATTATGAGAGGAGCCTTCATGAGATTAATGTGTATGATCTACTTTGTAAAAGACCATGGTTGTGTCCAAGTAAAACCACACAATATTT
ACTCTACTGATTGTGACGTCAATGTAATGTTCTTCTACCTTTGTACTTTCTACATATCCTACACTATCCAGACTTCGTGAATCTTGTTTTACACATCTTGATGGTTTTCACTGA
CTGCCTTCAGCTGAAAATGAAAAATGAAAAGTCAGCCTTGACTTGTTTCACAATATCCTACACTATCCAGACTTCGTGAATCTTGTTTTACACATCTTGATGGTTTTCACTGA
TGGATGCTTTGTCTGCAGCCTTGACTTGTTTCACAATATCCTACACTATCCAGACTTCGTGAATCTTGTTTTACACATCTTGATGGTTTTCACTGA
GATCTGACTCTATTGGAAAGTCAGTCGAGCTCAGCTCCTGTGATCTGGTGAAGATCATCACTCTTGAAACGTTACTGTTCTCCTCCCCCATTCCGTTAGGTTTCTGCCCA

Figure 6b (A) *Mus musculus* AAC-11$_{long}$ polynucleotide sequence [SEQ ID NO:1], cont'd.

ACACATGGAGAGAGTTAAGAGCAGTCTTAACCTTCTGCTTTCATTGTTTCTAAGGAAGCTGCTAGGCAGTGTTGTCGCATTCCTGCCAAGTCATAGAAATG
AAGCACCAGCTTCTCACAGTGTACAGGCGATGCCAGCCTTTTAGAAAGAACTTGCTTTGCATTGCCCCTTCAGTCTCTCCATATTTGGGATACAGCTTTGA
ACACAGGGTCTTATTATTTGAATAGGAGTACATGTGCATAATATACGTACAGACATAAGCATATGTGTGTATATATGCATGGAACTTGAGTGTACAAC
CAATCAATACATTAAATTCTCGGAAGGGTCCTCTGACATAGCGATTATCCCTTTGAGGCTGAATCCATTACTGACTTGGTATCTAGGTTTCACTCCAGTAG
GGAGGAATTTCAGTCAGCTGAACTTACAGATTATTATTGTGTTTAAAAACTAAAAAAACAAAGGCTGTTTTACAGAGACAAATTTAAAGACCCTGTTGGTGA
AATACAGCCAGATCTGGTGTACATACAGGTTCCCACAGGATCTGCTATGTAAGTGTTAGGATTTGGGAGACTTAAATAACCAGGGCTACCCCAAGAAATGTGAC
TTGGTGACATAGTACCATAAAAATTGCTCACTTCCGCTTGGCTTTTTGCCACTTTCAAATTTTAACTTCTCAGTTATTAATCAGATTATTGTGTAAGTTAGC
CAATAGTCTTTAGATTAAGGCAACAGACGGGAGTTCGTGGAGTGTCTCATTGTGGGCATTTTTAGTAGCCCAGACTCTGTCTTCATTTGAATGTTTCACAC
ATTTTTGTTCACAGTTAATCTTCCAAGTTTACTATTCAAGATTCAGAATTTACATTTCTAGTGGTTTGCTGTTTTTTATGTTTTTGGTTTTT
TTTGAGGTTTCATTTCTTACACAGGTGTTTTCATCACCATCAATTTTACACTGGGGGAAAAAAACAATTCCTTTGTGAGAATCACTGCAAGTATTTATGGCGAAA
ATATTTTGAAAGTTTAGGTGAAGCTGAACAGAGTGAACAGACATAGGAACATGGGATTGCCAGCTGAATCCTGTGACCATTTAGTTATGGACCTCACAAGCCTGAGCTGA
ACCTAGGCTCCCTTGGAAGCTGAACAGTGAACAGAGTAACATAAATTGAACACAGTAACTTTTCCTCTTTGCCTGAAGGCATTTGTAAACTCGGCAGAAGT
AAAGCCATTTCAAGTACAAAAATGAATTGGACTATAGCAACATAAATTGAACACAGTAACTTTTCCTCTTTGCCTGAAGGCATTTGTAAACTCGGCAGAAGT
AACTTGACCTCATGTCTCGAGAGCTCACTGCCATTCACCCCTCCTTTGCTTCCTTCCTCATCCTTTGCCTAGTCAGTAGTTCATAACTTAGTGTTCCTTT
TGCTTCAGAAATCTGAAAGAAAATCTTCATGCCATCAATCTTTTCTCCCGCAAGGACACCTGTGTCTCCCTGTTTAAATAAATGTAAATGCTCCCTTATGC
TTTGAAATAAATTCCTTTTGTAAAAAAAAAAAAAAAAAAAAAAAAAAAAAAAAAAAAAAAAAAAAAAAAAAAAAAAAAAAAAAAAAAAAAAAAAAAAAAAA
AAAAAAAAAA-3'

Figure 7

(B) *Mus musculus* AAC-11$_{long}$ polypeptide sequence deduced from a AAC-11$_{long}$ polynucleotide sequence in this table [SEQ ID NO:2].

NH$_2$-MPTVEELYRNYGILADATEQVGQHKDAYQVILDGVKGGTKEKRLAAQFIPKFFKHFPELADSAINAQLDLCEDEDVSIRRQAIKELPQFATGENLPRVA
DILTQLLQTDDSAEFNLVNNALLSIFKMDAKGTLGGLFSQILQGEDIVRERAIKFLSTKLKTLPDEVLTKEVEELILTESKKVLEDVTGEEFVLFMKILSGLK
SLQTVSGRQQLVELVAEQADLEQAFSPSDPDCVDRLLQCTRQAVPLFSKNVHSTRFVTYFCEQVLPNLSTLTTPVEGLDIQLEVLNLLAEMSSFCGDMEKLET
NLRKLFDKLLEYMPLPPEEAENGENAGNEEPKLQFSYVECLLYSFHQLGRKLPDFLTAKLNAEKLKDFKIRLQYFARGLQVYIRQLRLALQGKTGEALKTEEN
KIKVVALKITNNINVLIKDLFHIPPSYKSTVTLSWKPVQKVEIGQKRTSEDTSSGSPPKKSPGGPKRDARQIYNPPSGKYSSNLSNFNYERSLQGK*-COOH

Figure 8

(C) *Mus musculus* AAC-11$_{long}$ polypeptide sequence deduced from a AAC-11$_{long}$ polynucleotide sequence in this table [SEQ ID NO:3].

NH$_2$-MDAKGTLGGLFSQILQGEDIVRERAIKFLSTKLKTLPDEVLTKEVEELILTESKKVLEDVTGEEFVLFMKILSGLKSLQTVSGRQQLVELVAEQADLEQ
AFSPSDPDCVDRLLQCTRQAVPLFSKNVHSTRFVTYFCEQVLPNLSTLTTPVEGLDIQLEVLNLLAEMSSFCGDMEKLETNLRKLFDKLLEYMPLPPEEAENG
ENAGNEEPKLQFSYVECLLYSFHQLGRKLPDFLTAKLNAEKLKDFKIRLQYFARGLQVYIRQLRLALQGKTGEALKTEENKIKVVALKITNNINVLIKDLFHI
PPSYKSTVTLSWKPVQKVEIGQKRTSEDTSSGSPPKKSPGGPKRDARQIYNPPSGKYSSNLSNFNYERSLQGK*-COOH

Figure 9

(D) *Homo sapiens* AAC-11$_{long}$ polypeptide sequence [SEQ ID NO:4].

NH$_2$-MPTVEELYRNYGILADATEQVGQHKDAYQVILDGVKGGTKEKRLAAQFIPKFKHFPELADSAINAQLDLCEDEDVSIRRQAIKELPQFATGENLPRVA
DILTQLLQTDDSAEFNLVNNALLSIFKMDAKGTLGGLFSQIIQGEDIVRERAIKFLSTKLKTLPDEVLTKEVEELILTESKKVLEDVTGEEFVLFMKILSGLK
SLQTVSGRQQLVELVAEQADLEQTFNPSDPDCVDRLLQCTRQAVPLFSKNVHSTRFVTYFCEQVLPNLGTLTTPVEGLDIQLEVLNLLAEMSSFCGDMEKLET
NLRKLFDKLLEYMPLPPEEAENGENAGNEEPKLQFSYVECLLYSFHQLGRKLPDFLTAKLNAEKLHESKIRLQYFARGLQVYIRQLRLALQGKTGEALKTEEN
KIKVVALKITNNINVLIKDLFHIPPSYKSTVTLSWKPVQKVEIGQKRASEDTTSGSPPKKSSAGPKRDARQIYNLPSGKYSSNLSNFNYERSLQGK*-COOH

Figure 10

(E) *Mus musculus* AAC-11$_{short}$ polynucleotide sequence [SEQ ID NO:5].

5'-ACAAGATTTGTGACGTATTCTGTGAGCAAGTTCTCCCTAACCTCAGCACCCTGACCACCCCAGTGGAAGCCTCGATATACAGCTGGAGGTATTAAATT
TGTTGGCAGAGATGAGTTCATTTTGTGGTGACATGGAGAGAAAAACTAGAAACAAATTTAAGAAAACTGTTGATAAGTTATTGGAGTATATGCCTCTCCAGA
AGAAGCAGAAAATGGGGAGAATGCTGGTAATGAGGAGCCCAAGCTGCAGTTCAGTTATGTGAGTGCTTATTGTACAGTTTCATCAGTTGGGCGAAAACTT
CCAGACTTCTTAACAGCCAAACTGAATGCAGAAAAACTCAAGGATTTCAAAATTAGGTTGCAGTACTTTGCACGGGGCCTGCAGGTTTATATCAGACAACTTC
GCTTGGCTCTCCAGGTAAAACAGGCGAGGCCTTAAAAACAGAGGAGAACAAGATAAAAGTTGTTGCACTGAAAATAACAATATCAATGTTTAATCAA
GGATCTCTTCCACATTCCTCCTTCTTATAAGACCACAGTAACATTGTCCTGGAAACCTGTGCAGAAAGTTGAGATTGGCAAAAGAGAACCAGTGAAGATACA
AGTTCAGTTCACCACCTAAGAAGTCTCCAGGAGAACAAAAGAGATGCCAGACAGATTATAATCCTCCAGTGGAGAAGTACAGCAGCAATCTGAGCAACT
TTAATTATGAGAGGAGCCTTCAGGGAAATAGAGGTGGCCGGAACACGAGGAAATCGAAGTCGAGGAAGACTCTACTGATTGTGACGTCACATTC
TTCAGCATTGTCATGAGATTAATATACTTAAATCTACTACTCATTGGATTGCCGGGATGTCCCTTTAAAAGGACTGCTGCTTCAGCTGAAATGTAATGTT
CTTTCTACCTTTGTATGTATGATCTACTTTTGTAAAAGACCAATGGTTGTGTCCAAGGTAAAACCACAACAATATTTTTGGATGCTT-3'

Figure 11

(F) *Mus musculus* AAC-11<sub>short</sub> polypeptide sequence deduced from a polynucleotide sequence in this table [SEQ ID NO:6].

NH2-MSSFCGDMEKLETNLRKLFDKLLEYMPLPPEEAENGENAGNEEPKLQFSYVECLLYSFHQLGRKLPDFLTAKLNAEKLKDFKIRLQYFARGLQVYIRQLRLALQGKTGEALKTEENKIKVVALKITNNINVLIKDLFHIPPSYKSTVTLSWKPVQKVEIGQKRTSEDTSSGSPPKKSPGGPKRDARQIYNPPSGKYSSNLSNFNYERSLQGK*-COOH

Figure 12

(G) *Mus musculus* AAC-11<sub>short</sub> polypeptide sequence deduced from a polynucleotide sequence in this table [SEQ ID NO:7].

NH2-MEKLETNLRKLFDKLLEYMPLPPEEAENGENAGNEEPKLQFSYVECLLYSFHQLGRKLPDFLTAKLNAEKLKDFKIRLQYFARGLQVYIRQLRLALQGKTGEALKTEENKIKVVALKITNNINVLIKDLFHIPPSYKSTVTLSWKPVQKVEIGQKRTSEDTSSGSPPKKSPGGPKRDARQIYNPPSGKYSSNLSNFNYERSLQGK*-COOH

Figure 13

(H) *Homo sapiens* AAC-11<sub>short</sub> polypeptide sequence [SEQ ID NO:8].

NH2-MSSFCGDMEKLETNLRKLFDKLLEYMPLPPEEAENGENAGNEEPKLQFSYVECLLYSFHQLGRKLPDFLTAKLNAEKLHESKIRLQYFARGLQVYIRQLRLALQGKTGEALKTEENKIKVVALKITNNINVLIKDLFHIPPSYKSTVTLSWKPVQKVEIGQKRASEDTTSGSPPKKSSAGPKRDAROIYNLPSGKYSSNLSNFNYERSLQGK*-COOH

Figure 14

(I) *Homo sapiens* AAC-11short polypeptide sequence [SEQ ID NO:9].

NH2-MEKLETNLRKLFDKLLEYMPLPPEEAENGENAGNEEPKLQFSYVECLLYSFHQLGRKLPDFLTAKLNAEKLHESKIRLQYFARGLQVYIRQLRLALQGK
TGEALKTEENKIKVVALKITNNINVLIKDLFHIPPSYKSTVTLSWKPVQKVEIGQKRASEDTTSGSPPKKSSAGPKRDARQIYNLPSGKYSSNLSNFNYERSL
QGK*-COOH

COMPOSITIONS AND METHODS FOR MODULATING APOPTOSIS

This application claims benefit of U.S. Provisional Application No. 60/071,878, filed Jan. 20, 1998.

This invention was made in the course of research sponsored by the National Institutes of Health. The U. S. Government may have certain rights in this invention.

This invention relates to newly identified polynucleotides and polypeptides, and their production and uses, as well as their variants, agonists and antagonists, and their uses. In particular, the invention relates to polynucleotides and polypeptides of the AAC-11 (antiapoptosis clone-11) family, hereinafter referred to as "AAC-11".

Programmed cell death, or apoptosis, plays a critical role in development, tissue renewal and repair, and tumor growth (Thompson. C.B. *Science* 1995, 267:1456–1462; Stewart, B. W. *J. Natl. Cancer Inst.* 1994, 86:1286–1296). Apoptosis may be induced directly by a host of physiological or nonphysiological signals including tumor necrosis factor, FAS ligand, oxidative stress, and viruses. Alternatively, apoptosis occurs after removal of extracellular growth factors, cytokines, or attachment substrata or by the inappropriate expression of cell cycle components. The latter observations suggest that apoptosis in proliferating cells reflects a conflict in the cell cycle or a default pathway in cell cycle progression that is diverted by specific intracellular factors (Evan et al. *Curr. Opin. Cell Biol.* 1995, 7:825–834; Meikrantz, W. and R. Schlegel *J. Cell. Biochem.* 1995, 58:160–174). Viewed differently, cellular viability is dependent on the functional balance of factors that favor apoptosis versus extracellular (e.g., growth factors) and intracellular survival signals. Examples of such survival factors include bcl-2 and related family members (Yang, E. and S. J. Korsmeyer *Blood* 1996, 88:386–401), proteins that inhibit tumor necrosis factor killing such as MnSOD (Wong et al. *Cell* 1989, 58:923–931), A20 (Opipari et al. *J. Biol. Chem.* 1992, 267:12424–12427), and plasminogen activator inhibitor 2 (Kroemer et al. *FASEB J.* 1995, 9:1277–1287; Dickinson et al. *J. Biol. Chem.* 1995. 270:27894–27904), as well as recently identified proteins such as calcium-binding protein ALG-2 (Vito et al. *Science* 1996, 271:521–525) and mammalian homologues of baculovirus IAP gene (Liston et al. *Nature* 1996, 379:349–353; Hay et al. *Cell* 1995, 83: 1253–1262; Duckett et al. *EMBO J.* 1996, 15:2685–2694).

Many growth factors and cytokines act as cellular survival factors by preventing apoptosis. However, the specific genes and corresponding proteins that mediate cell survival are poorly defined. For example insulin-like growth factor I (IGF-I) prevents apoptosis in diverse settings, including deprivation of growth factors and cytokines (Barres et al. *Cell* 1992, 70:31–46; Rodriguez-Tarduchy et al. *J. Immunol.* 1992, 149:535–540), cell cycle dysregulation (Harrington et al. *EMBO J.* 1994, 13:3286–3295; Sell et al. *Cancer Res.* 1995, 55:303–306), ischemia (Buerke et al. *Proc. Natl. Acad. Sci. USA* 1995, 92:8031–8035), administration of tumor necrosis factor, hyperosmotic shock (Matthews. C. C. and Feldman. E. L. *J. Cell Physiol.* 1996, 166:323–331), and activation of IL-lb-converting enzyme (Yong-Kuen et al. *J. Biol. Chem.* 1996, 271:5112–5117). However, the mechanism by which the activated IGF-I receptor inhibits apoptosis is unknown. For growth factor-regulated cells such as murine fibroblasts, long-term survival in the presence of IGF-I does require continuous gene expression (Tamm, I. and Kikuchi, T. *J. Cell. Physiol.* 1990, 143:494–500). IGF-I modulates gene expression both transcriptionally and for survival by stabilizing existing mRNA transcripts (Zumstein, P. and Stiles C. D. *J. Biol. Chem.* 1987 262:11252–11260).

In a more recent publication by Ambrosini et al., a new anti-apoptosis gene referred to as "survivin" is disclosed (Ambrosini, G. et al. *Nat. Med.* 1997. 3:917–921). This gene encodes a 16.5 kDa protein and is found in more than 50% of non-Hodgkin's lymphomas examined. The mRNA detected was 1.9 kb.

A novel cDNA has now been isolated and is referred to herein as antiapoptosis clone 11 (AAC-11). This clone expresses a 25 kDa protein that prevents apoptosis caused by deprivation of growth factors in a cell.

SUMMARY OF THE INVENTION

The present invention relates to AAC-11 in particular AAC-11 polypeptides and AAC-11 polynucleotides, recombinant materials and methods for their production. In another aspect, the present invention relates to methods for using such polypeptides and polynucleotides, including methods of inhibiting apoptosis in a cell. In a further aspect, the present invention relates to identifying agonists and antagonists using the materials provided by the invention. In still a further aspect, the present invention relates to compositions and methods for inhibiting apoptosis in a cell, preferably an animal cell, most preferably a human cell. In another aspect, the present invention relates to a method of inhibiting apoptosis in a cell, preferably an animal cell, most preferably a human cell, wherein an effective amount of a protein encoded by a AAC-11 polynucleotide so that apoptosis in the cell is inhibited. In another aspect, the present invention relates to a method of inhibiting apoptosis in a cell, preferably an animal cell, most preferably a human cell, wherein an effective amount of a AAC-11 polynucleotide is administered to the cell so that the cell encodes the polynucleotide thereby inhibiting apoptosis in the cell. In yet a further aspect, the present invention relates to compositions and methods for inducing apoptosis in a cell by inhibiting expression of the AAC-11 polynucleotides or the activity of the AAC-11 polypeptides encoded thereby.

BRIEF DESCRIPTION OF THE DRAWINGS

FIGS. 1A and 1B shows the nucleic acid and deduced amino acid sequences of the AAC-11$_{long}$ and AAC-11$_{short}$ species. Predicted human amino acid sequences, where different from mouse, are presented below the corresponding mouse sequences. The nucleotide sequence has been deposited in GenBank (accession number U35846 for mouse cDNA and U93857 for human cDNA). Nucleotide sequence numbers are on the right. AAC-11$_{short}$ cDNA sequences are underlined. A polyadenylic acid tail (14 bp) of AAC-11$_{short}$ begins at bp 185 1 (↑). Potential methionine start sites (→) N-linked glycosylation sites (double underlined) protein kinase C (+) and tyrosine kinase (underlined) phosphorylation sites, and leucine repeat with terminal lysine (↑) are indicated. AATAAA polyadenylation sites are shown in bold italic.

FIGS. 6a–6b shows the nucleotide sequence of Mus musculus AAC-11$_{long}$ (SEQ ID NO:1).

FIG. 7 shows a Mus musculus AAC-11$_{long}$ polypeptide sequence (SEQ ID NO:2).

FIG. 8 shows another Mus musculus AAC-11$_{long}$ polypeptide sequence (SEQ ID NO:3) deduced from SEQ ID NO:1.

FIG. 9 shows a Homo sapiens AAC-11$_{long}$ polypeptide sequence (SEQ ID NO:4).

FIG. 10 shows the nucleotide sequence of Mus musculus AAC-11$_{short}$ (SEQ ID NO:5).

FIG. 11 shows a Mus musculus AAC-11$_{short}$ polypeptide sequence (SEQ ID NO:6).

FIG. 12 shows another Mus musculus AAC-11$_{short}$ polypeptide sequence (SEQ ID NO:7).

FIG. 13 shows a Homno sapiens AAC-11$_{short}$ polypeptide sequence (SEQ ID NO:8).

FIG. 14 shows another Homo sapiens AAC-11$_{short}$ polypeptide sequence (SEQ ID NO:9).

DETAILED DESCRIPTION OF THE INVENTION

Figure 2:
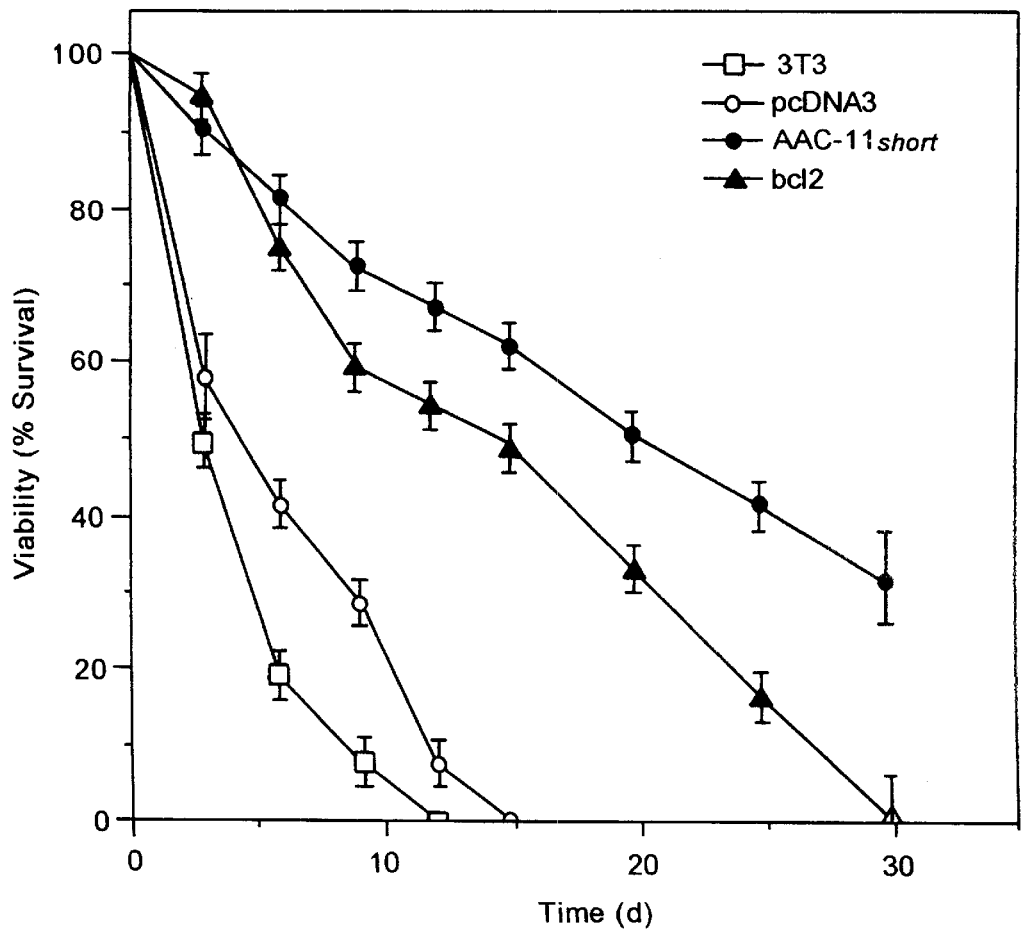
FIG. 2 is a graph showing the time course of wild-type BALB/c3T3 cell death in a serum-free medium as the number of viable cells expressed as a percentage of the cells before the removal of serum as a function of time and represent the mean±SE of triplicate determinations from one of at least three experiments, wherein the cells have been transfected with AAC-11$_{short}$.

The present invention relates to AAC-11 polypeptides and polynucleotides as described in greater detail below. U.S. Provisional Application No. 60/071,878 is incorporated by reference herein in its entirety. In particular, the present invention relates to polypeptides and polynucleotides which play a role in the regulation of apoptosis. The present invention relates especially to AAC-11 polynucleotides and polypeptide having the nucleotide and amino acid sequences set forth in SEQ ID NO:1 or 5 and SEQ ID NO:2 or 3 or 4 or 6 or 7 or 8 or 9, respectively. Note that sequences recited in the Sequence Listing below as "DNA" represent an exemplification of the present invention, since those of ordinary skill will recognize that such sequences can be usefully employed in polynucleotides in general, including ribopolynucleotides.

Polypeptides

In one aspect of the invention there are provided polypeptides of Mus musculus and Homo sapiens referred to herein as "AAC-11" and "AAC-11 polypeptides" as well as biologically, diagnostically, prophylactically, clinically or therapeutically useful variants thereof, and compositions comprising the same.

Among the particularly preferred embodiments of the invention are variants of AAC-11 polypeptide encoded by naturally occurring alleles of the AAC-11 gene.

The present invention further provides for an isolated polypeptide which: (a) comprises or consists of an amino acid sequence which has at least 70% identity, preferably at least 80% identity, more preferably at least 90% identity yet more preferably at least 95% identity, most preferably at least 97–99% or exact identity, to that of SEQ ID NO:2 or 3 or 4 or 6 or 7 or 8 or 9 over the entire length thereof; (b) a polypeptide encoded by an isolated polynucleotide comprising or consisting of a polynucleotide sequence which has at least 70% identity, preferably at least 80% identity, more preferably at least 90% identity, yet more preferably at least 95% identity, even more preferably at least 97–99% or exact identity to SEQ ID NO:1 over the entire length of SEQ ID NO:1; or (c) a polypeptide encoded by an isolated polynucleotide comprising or consisting of a polynucleotide sequence encoding a polypeptide which has at least 70% identity, preferably at least 80% identity, more preferably at least 90% identity, yet more preferably at least 95% identity, even more preferably at least 97–99% or exact identity, to the amino acid sequence of SEQ ID NO:2 or 3 or 4 or 6 or 7 or 8 or 9, over the entire length thereof.

The polypeptides of the invention include a polypeptide of SEQ ID NO:2 or 3 or 4 or 6 or 7 or 8 or 9 (in particular the mature polypeptide) as well as polypeptides and fragments, particularly those which have the biological activity of AAC-11, and also those which have at least 70% identity to a polypeptide of SEQ ID NO:2 or 3 or 4 or 6 or 7 or 8 or 9 or the relevant portion, preferably at least 80% identity to a polypeptide of SEQ ID NO:2 or 3 or 4 or 6 or 7 or 8 or 9 and more preferably at least 90% identity to a polypeptide of SEQ ID NO:2 or 3 or 4 or 6 or 7 or 8 or 9 and still more preferably at least 95% identity to a polypeptide of SEQ ID NO:2 or 3 or 4 or 6 or 7 or 8 or 9 and also include portions of such polypeptides with such portion of the polypeptide generally containing at least 30 amino acids and more preferably at least 50 amino acids.

The invention also includes a polypeptide consisting of or comprising a polypeptide of the formula:

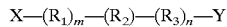

$$X—(R_1)_m—(R_2)—(R_3)_n—Y$$

wherein, at the amino terminus, X is hydrogen, a metal or any other moiety described herein for modified polypeptides, and at the carboxyl terminus, Y is hydrogen, a metal or any other moiety described herein for modified polypeptides, $R_1$ and $R_3$ are any amino acid residue or modified amino acid residue, m is an integer between 1 and 1000 or zero, n is an integer between 1 and 1000 or zero, and $R_2$ is an amino acid sequence of the invention, particularly an amino acid sequence selected from SEQ ID NOs:2–4 and 6–9 or modified forms thereof In the formula above. $R_2$ is oriented so that its amino terminal amino acid residue is at the left, covalently bound to $R_1$, and its carboxy terminal amino acid residue is at the right, covalently bound to $R_3$. Any stretch of amino acid residues denoted by either $R_1$ or $R_3$, where m and/or n is greater than 1, may be either a heteropolymer or a homopolymer, preferably a heteropolymer. Other preferred embodiments of the invention are provided where m is an integer between 1 and 50, 100 or 500, and n is an integer between 1 and 50, 100, or 500.

It is most preferred that a polypeptide of the invention is derived from Mus musculus or Homo sapiens, however, it may preferably be obtained from other organisms of the same taxonomic genus. A polypeptide of the invention may also be obtained, for example, from organisms of the same taxonomic family or order.

A fragment is a variant polypeptide having an amino acid sequence that is entirely the same as part but not all of any amino acid sequence of any polypeptide of the invention. As with AAC-11 polypeptides, fragments may be "free-standing," or comprised within a larger polypeptide of which they form a part or region, most preferably as a single continuous region in a single larger polypeptide.

Preferred fragments include, for example, truncation polypeptides having a portion of an amino acid sequence of SEQ ID NO:2 or 3 or 4 or 6 or 7 or 8 or 9, or of variants thereof, such as a continuous series of residues that includes an amino- and/or carboxyl-terminal amino acid sequence. Degradation forms of the polypeptides of the invention produced by or in a host cell, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Further preferred fragments include an isolated polypeptide comprising an amino acid sequence having at least 15, 20, 30, 40, 50 or 100 contiguous amino acids from the amino acid sequence of SEQ ID NO:2 or 3 or 4 or 6 or 7 or 8 or 9, or an isolated polypeptide comprising an amino acid sequence having at least 15, 20, 30, 40, 50 or 100 contiguous amino acids truncated or deleted from the amino acid sequence of SEQ ID NO:2 or 3 or 4 or 6 or 7 or 8 or 9.

Also preferred are biologically active fragments that are those fragments that mediate activities of AAC-11, including those with a similar activity, or an improved activity, or Kith a decreased undesirable activity.

Fragments of the polypeptides of the invention may be employed for producing the corresponding full-length polypeptide by peptide synthesis; therefore, these variants may be employed as intermediates for producing the full-length polypeptides of the invention.

Polynucleotides

It is an object of the invention to provide polynucleotides that encode AAC-11 polypeptides, particularly polynucleotides that encode the polypeptides herein designated AAC-$11_{short}$.

In a particularly preferred embodiment of the invention the polynucleotide has a region encoding AAC-11 polypeptides comprising a sequence set out in SEQ ID NO:1 or 5 which includes a full length gene, or a variant thereof. This full length genie encodes polypeptides that are capable of increasing the survival of cells through inhibition of apoptosis.

As a further aspect of the invention there are provided isolated nucleic acid molecules encoding and/or expressing AAC-11 polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a AAC-11 polypeptide having a deduced amino acid sequence of SEQ ID NO:2 or 3 or 4 or 6 or 7 or 8 or 9 and polynucleotides closely related thereto and variants thereof.

In another particularly preferred embodiment of the invention there is a AAC-11 polypeptide from Mus musculus or Homo sapiens having an amino acid sequence of SEQ ID NO:2 or 3 or 4 or 6 or 7 or 8 or 9, or a variant thereof.

Using the information provided herein, such as a polynucleotide sequence set out in SEQ ID NO:1 or 5, a polynucleotide of the invention encoding AAC-11 polypeptide may be obtained using standard cloning and screening methods. For example, to obtain a polynucleotide sequence of the invention, such as a polynucleotide sequence given in SEQ ID NO:1 or 5, typically a library of clones of chromosomal DNA is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed., Cold Spring Harbor Laboratory Press. Cold Spring Harbor, N.Y. (1989). (see in particular Screening By Hybridization 1.90 and Sequencing Denatured Double-Stranded DNA Templates 13.70). Direct genomic DNA sequencing may also be performed to obtain a full length gene sequence.

Moreover, the DNA sequences set forth in SEQ ID NOs:1 and 5 contain an open reading frame encoding a protein having about the number of amino acid residues set forth in SEQ ID NO:2 or 3 or 6 or 7 with a deduced molecular weight that can be calculated using amino acid residue molecular weight values well known to those skilled in the art. A preferred embodiment of the invention is a polynucleotide having nucleotides 1 to 636 set forth in SEQ ID NO:5, which encodes the AAC-$11_{short}$ polypeptides set forth in SEQ ID NO:6 or 7.

In a further aspect, the present invention provides for an isolated polynucleotide comprising or consisting of (a) a polynucleotide sequence which has at least 70% identity, preferably at least 80% identity, more preferably at least 90% identity, yet more preferably, at least 95% identity, even more preferably at least 97–99%, still more preferably greater than 99%. yet still more preferably at least 99.5% or exact identity to SEQ ID NO:1 or 5 over the entire length thereof, or the entire length of that portion of SEQ ID NO:1 or 5 which encodes SEQ ID NO:2 or 3 or 6 or 7; (b) a polynucleotide sequence encoding a polypeptide which has at least 70% identity, preferably at least 80% identity, more preferably at least 90% identity, yet more preferably at least 95% identity, even more preferably at least 97–99% or 100% exact, to the amino acid sequence of SEQ ID NO:2 or 3 or 4 or 6 or 7 or 8 or 9, over the entire length thereof.

A polynucleotide encoding a polypeptide of the present invention, including homologs and orthologs from species other than *Mus musculus* and *Homo sapiens*, may be obtained by a process which comprises the steps of screening an appropriate library under stringent hybridization conditions Kith a labeled or detectable probe consisting of or comprising the sequence of SEQ ID NO:1 or 5 or a fragment thereof, and isolating a full-length gene and/or genomic clones containing said polynucleotide sequence.

The invention provides a polynucleotide sequence identical over its entire length to a coding sequence (open reading frame) of the nucleic acid sequence set forth in SEQ ID NO:1 or 5. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or prepro-protein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals) ribosome binding sites, Kozak sequences, that stabilize mRNA, introns, and polyadenylation signals. The polynucleotide sequence may also comprise additional coding sequence encoding additional aminio acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821–824 (1989), or an HA peptide tag (Wilson et al., *Cell* 37: 767 (1984), both of which may be useful in purifying polypeptide sequence fused to them. Polynucleotides of the invention also include, but are not limited to, polynucleotides comprising a structural gene and its naturally associated sequences that control gene expression.

A preferred embodiment of the invention is a polynucleotide having nucleotides 1 to the nucleotide immediately upstream of or including nucleotide 637 set forth in SEQ ID NO:5, both of which encode the AAC-11$_{short}$ polypeptide set forth in SEQ ID NO:6 or 7.

The invention also includes a polynucleotide consisting of or comprising a polynucleotide of the formula:

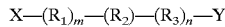

wherein, at the 5' end of the molecule, X is hydrogen, a metal or a modified nucleotide residue, or together with Y defines a covalent bond and at the 3' end of the molecule, Y is hydrogen, a metal, or a modified nucleotide residue, or together with X defines the covalent bond, each occurrence of $R_1$ and $R_3$ is independently any nucleic acid residue or modified nucleic acid residue, m is an integer between 1 and 3000 or zero, n is an integer between 1 and 3000 or zero, and $R_2$ is a nucleic acid sequence or modified nucleic acid sequence of the invention, particularly a nucleic acid sequence selected from SEQ ID NOs:1 and 5 or a modified nucleic acid sequence thereof. In the polynucleotide formula above, $R_2$ is oriented so that its 5' end nucleic acid residue is at the left, bound to $R_1$, and its 3' end nucleic acid residue is at the right, bound to $R_3$. Any stretch of nucleic acid residues denoted by either $R_1$ and/or $R_2$, where in and/or n is greater than 1, may be either a heteropolymer or a homopolymer, preferably a heteropolymer. Where, in a preferred embodiment, X and Y together define a covalent bond, the polynucleotide of the above formula is a closed, circular polynucleotide, which can be a double-stranded polynucleotide wherein the formula shows a first strand to which the second strand is complementary. In another preferred embodiment m and/or n is an integer between 1 and 1000. Other preferred embodiments of the invention are provided where m is an integer between 1 and 50, 100 or 500, and n is an integer between 1 and 50, 100, or 500.

It is most preferred that a polynucleotide of the invention is derived from *Mus musculus* or *Homo sapiens*, however it may preferably be obtained from other organisms of the same taxonomic genuses. A polynucleotide of the invention may also be obtained, for example, from organisms of the same taxonomic families or orders.

The term "polynucleotide encoding a polypeptide" as used herein encompasses polynucleotides that include a sequence encoding a polypeptide of the invention, more particularly a polypeptide having an amino acid sequence set out in SEQ ID NO:2 or 3 or 4 or 6 or 7 or 8 or 9. The term also encompasses polynucleotides that include a single continuous region or discontinues regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of SEQ ID NO:2 or 3 or 4 or 6 or 7 or 8 or 9. Fragments of polynucleotides of the invention may be used, for example, to synthesize full-length polynucleotides of the invention.

Further particularly preferred embodiments are polynucleotides encoding AAC-11 variants, that have the amino acid sequence of AAC-11 polypeptide of SEQ ID NO:2 or 3 or 4 or 6 or 7 or 8 or 9 in which several, a few, 5 to 10, 1 to 5, to 3,2,1 or no amino acid residues are substituted, modified, deleted and/or added, in any combination, Especially preferred among these are silent substitutions, additions and deletions, that do not alter the properties and activities of AAC-11 polypeptide.

Further preferred embodiments of the invention are polynucleotides that are at least 70% identical over their entire length to a polynucleotide encoding AAC-11 polypeptide having an amino acid sequence set out in SEQ ID NO:2 or 3 or 4 or 6 or 7 or 8 or 9, and polynucleotides that are complementary to such polynucleotides. Alternatively, most highly preferred are polynucleotides that comprise a region that is at least 80% identical over its entire length to a polynucleotide encoding AAC-11 polypeptide and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity, as the mature polypeptide encoded by a DNA of SEQ ID NO:1 or 5.

In accordance with certain preferred embodiments of this invention there are provided polynucleotides that hybridize, particularly under stringent conditions, to AAC-11 polynucleotide sequences, such as those polynucleotides set forth in SEQ ID NOs: 1 and 5.

The invention further relates to polynucleotides that hybridize to the polynucleotide sequences provided herein. In this regard the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml of denatured, sheared salmon spenn DNA, followed by washing the hybridization support in 0.1×SSC at about 65° C. Hybridization and wash conditions are well known and exemplified in Sambrook, el al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in SEQ ID NO:1 or 5 under stringent hybridization conditions with a probe having the sequence of said polynucleotide sequence set forth in SEQ ID NO:1 or 5 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding AAC-11 and to isolate cDNA and genomic clones of other genes that have a high identity, particularly high sequence identity, to the AAC-11 gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

A coding region of a AAC-11 gene may be isolated by screening using a DNA sequence provided in SEQ ID NO:1 or 5 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

There are several methods available and well known to those skilled in the art to obtain full-length DNAs, or extend short DNAs, for example those based on the method of Rapid Amplification of cDNA ends (RACE) (see, for example, Frohman, et al., *PNAS USA* 85: 8998–9002, 1988). Recent modifications of the technique, exemplified by the Marathon™ technology (Clontech Laboratories Inc.) for example have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the selected gene sequence). The products of this reaction can then be analyzed by DNA sequencing and a full-length DNA constructed either by joining the product directly to the existing DNA to give a complete sequence, or carrying out a separate full-length PCR using the new sequence information for the design of the 5' primer.

The polynucleotides and polypeptides of the invention may be employed, for example, as research reagents and materials for discovery of treatments of and diagnostics for diseases, particularly human diseases, as further discussed herein relating to polynucleotide assays.

The invention also provides polynucleotides that encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

For each and every polynucleotide of the invention there is provided a polynucleotide complementary to it. It is preferred that these complementary polynucleotides are fully complementary, to each polynucleotide with which they are complementary.

A precursor protein, having a mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

Vectors, Host Cells, Expression Systems

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

Recombinant polypeptides of the present invention may be prepared by processes well known to those skilled in the art from genetically engineered host cells comprising expression systems. Accordingly, in a further aspect, the present invention relates to expression systems that comprise a polynucleotide or polynucleotides of the present invention, to host cells which are genetically engineered with such expression systems, and to the production of polypeptides of the invention by recombinant techniques.

For recombinant production of the polypeptides of the invention, host cells can be genetically engineered to incorporate expression systems or portions thereof or polynucleotides of the invention. Introduction of a polynucleotide into the host cell can be effected by methods described in many standard laboratory manuals, such as Davis, et al., *BASIC METHODS IN MOLECULAR BIOLOGY*, (1986) and Sambrook. et al., *MOLECULAR CLONING: A LABORATORY MANUAL*, 2nd Ed., Cold Spring Harbor Laboratory Press. Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as cells of streptococcih staphylococci, enterococci, *E. coli*, streptomyces, cyanobacteria, *Bacillus subtilis*, and *Streptococcus pneuimoniae*; fungal cells, such as cells of a yeast, Kluveromyces, Saccharomyces, a basidiomycete, *Candida albicans* and Aspergillus; insect cells such as cells of Drosophila S2 and Spodoptera Sf9; animal cells such as CHO, COS, HeLa, C127, 3T3, BHK, 293, CV-1 and Bowes melanoma cells; and plant cells, such as cells of a gymnosperm or angiosperm.

A great variety of expression systems can be used to produce the polypeptides of the invention. Such vectors include, among others, chromosomal-, episomal- and virus-derived vectors, for example, vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, picornaviruses and retroviruses, and vectors derived from combinations thereof, such as those derived from plasmid and bacteriophage genetic elements, such as cosmids and phagcmids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook el al., *MOLECULAR CLONING, A LABORATORY MANUAL*, (supra).

In recombinant expression systems in eukaryotes, for secretion of a translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Most preferably, high performance liquid chromatography is employed for purification. Well known techniques for refolding protein may be employed to regenerate active conformation when the polypeptide is denatured during isolation and or purification.

Antibodies

The polypeptides and polynucleotides of the invention or variants thereof, or cells expressing the same can be used as immunogens to produce antibodies immunospecific for such polypeptides or polynucleotides respectively.

In certain preferred embodiments of the invention there are provided antibodies against AAC-11 polypeptides or polynucleotides.

Antibodies generated against the polypeptides or polynucleotides of the invention can be obtained by administering the polypeptides and/or polynucleotides of the invention, or epitope-bearing fragments of either or both, analogues of either or both, or cells expressing either or both, to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., *Nature* 256: 495–497 (1975): Kozbor et al., *Immunology Today* 4: 72 (1983). Cole et al., pg. 77–96 in *MONOCLONAL ANTIBODIES AND CANCER THERAPY*, Alan R. Liss, Inc. (1985).

Techniques for the production of single chain antibodies (U.S. Pat. No. 4,946,778) can be adapted to produce single chain antibodies to polypeptides or polynucleotides of this invention. Also, transgenic mice, or other organisms such as other mammals, may be used to express humanized antibodies immunospecific to the polypeptides or polynucleotides of the invention.

Alternatively, phage display technology may be utilized to select antibody genes with binding activities towards a polypeptide of the invention either from repertoires of PCR amplified v-genes of lymphocytes from humans screened for possessing anti-AAC-11 or from naive libraries (McCafferty, el al., (1990), *Nature* 348, 552–554: Marks, et al., (1992) *Biotechnology* 10, 779–783). The affinity of these antibodies can also be improved by, for example, chain shuffling (Clackson et al., (1991) *Nature* 352: 628).

The above-described antibodies may be employed to isolate or to identify clones expressing the polypeptides or polynucleotides of the invention to purify the polypeptides or polynucleotides by, for example, affinity chromatography.

Thus, among others, antibodies against AAC-11-polypeptide or AAC-11 polynucleotide may be employed to modulate the cell death pathway in degenerative diseases and in cancer.

Antagonists and Agonists—Assays and Molecules

Polypeptides and polynucleotides of the invention may also be used to assess the binding of substrates and ligands in, for example, cells, cell-free preparations, chemical libraries, and natural product mixtures. These substrates and ligands may be natural substrates and ligands or may be structural or functional mimetics. See, e.g., Coligan et al., *Current Protocols in Immunology* 1(2): Chapter 5 (1991).

Polypeptides and polynucleotides of the present invention inhibit apoptosis in cells. It is therefore desirable to devise screening methods to identify compounds which stimulate or which inhibit the function of the polypeptide or polynucleotide. Accordingly, in a further aspect, the present invention provides for a method of screening compounds to identify, those which stimulate or which inhibit the function of a polypeptide or polynucleotide of the invention, as well as related polypeptides and polynucleotides. In general, agonists or antagonists may be employed for therapeutic and prophylactic purposes for use in modulating the cell death pathway in degenerative diseases and in cancer. Compounds may be identified from a variety of sources, for example, cells, cell-free preparations chemical libraries, and natural product mixtures. Such agonists, antagonists or inhibitors so-identified may be natural or modified substrates, ligands, receptors, enzymes, etc., as the case may be, of AAC-11 polypeptides and polynucleotides; or may be structural or functional mimetics thereof (see Coligan et al., *Current Protocols in Immunology* 1(2):Chapter 5 (1991)).

The screening methods may simply measure the binding of a candidate compound to the polypeptide or polynucleotide, or to cells or membranes bearing the polypeptide or polynucleotide, or a fusion protein of the polypeptide by means of a label directly or indirectly associated with the candidate compound. Alternatively, the screening method may involve competition with a labeled competitor. Further, these screening methods may test whether the candidate compound results in a signal generated by activation or inhibition of the polypeptide or polynucleotide, using detection systems appropriate to the cells comprising the polypeptide or polynucleotide. Inhibitors of activation are generally assayed in the presence of a known agonist and the effect on activation by the agonist by the presence of the candidate compound is observed. Constitutively active polypeptide and/or constitutively expressed polypeptides and polynucleotides may be employed in screening methods for inverse agonists or inhibitors, in the absence of an agonist or inhibitor, by testing whether the candidate compound results in inhibition of activation of the polypeptide or polynucleotide, as the case may be. Further, the screening methods may simply comprise the steps of mixing a candidate compound with a solution containing a polypeptide or polynucleotide of the present invention to form a mixture, measuring AAC-11 polypeptide and/or polynucleotide activity in the mixture, and comparing the AAC-11 polypeptide and/or polynucleotide activity of the mixture to a standard. Fusion proteins, such as those made from FCC portion and AAC-11 polypeptide, as hereinbefore described, can also be used for high-throughput screening assays to identify antagonists of the polypeptide of the present invention, as well as of phylogenetically and/or functionally related polypeptides (see D. Bennett et al., J. Mol Recognition, 8:52–58 (1995); and K. Johanson et al., *J Biol Chem*, 270(16): 9459–9471 (1995)).

The polynucleotides, polypeptides and antibodies that bind to and/or interact with a polypeptide of the present invention may, also be used to configure screening methods for detecting the effect of added compounds on the production of mRNA and/or polypeptide in cells. For example, an ELISA assay may be constructed for measuring secreted or cell associated levels of polypeptide using monoclonal and polyclonal antibodies by standard methods knows in the art. This can be used to discover agents which may inhibit or enhance the production of polypeptide (also called antagonist or agonist, respectively) from suitably manipulated cells or tissues.

The invention also provides a method of screening compounds to identify those which enhance (agonist) or block (antagonist) the action of AAC-11 polypeptides or polynucleotides. The method of screening may involve high-throughput techniques. For example, to screen for agonists or antagonists, a synthetic reaction mix, a cellular compartment, such as a membrane, cell envelope or cell wall, or a preparation of any thereof, comprising AAC-11 polypeptide and a labeled substrate or ligand of such polypeptide is incubated in the absence or the presence of a candidate molecule that may be a AAC-11 agonist or antagonist. The ability of the candidate molecule to agonize or antagonize the AAC-11 polypeptide is reflected in decreased binding of the labeled ligand or decreased production of product from such substrate. Molecules that bind gratuitously, i.e., without inducing the effects of AAC-11 polypeptide are most likely to be good antagonists. Molecules that bind well and, as the case may be, increase the rate of product production from substrate, increase signal transduction, or increase chemical channel activity are agonists. Detection of the rate or level of, as the case may be, production of product from substrate, signal transduction, or chemical channel activity may be enhanced by using a reporter system. Reporter systems that may be useful in this regard include but are not limited to colorimetric, labeled substrate converted into product, a reporter gene that is responsive to changes in AAC-11 polynucleotide or polypeptide activity, and binding assays known in the art.

Polypeptides of the invention may be used to identify membrane bound or soluble receptors, if any, for such polypeptide, through standard receptor binding techniques known in the art. These techniques include, but are not limited to, ligand binding and crosslinking assays in which the polypeptide is labeled with a radioactive isotope (for instance, $^{125}$I), chemically, modified (for instance, biotinylated), or fused to a peptide sequence suitable for detection or purification, and incubated with a source of the putative receptor (e.g., cells, cell membranes, cell supernatants, tissue extracts, bodily materials). Other methods include biophysical techniques such as surface plasmon resonance and spectroscopy. These screening methods may also be used to identify agonists and antagonists of the polypeptide which compete with the binding of the polypeptide to its receptor(s) if any. Standard methods for conducting such assays are well understood in the art.

The fluorescence polarization value for a fluorescently-tagged molecule depends on the rotational correlation time or tumbling rate. Protein complexes, such as formed by AAC-11 polypeptide associating with another AAC-11 polypeptide or other polypeptide, labeled to comprise a fluorescently-labeled molecule will have higher polarization values than a fluorescently labeled monomeric protein. It is preferred that this method be used to characterize molecules that disrupt polypeptide complexes.

Fluorescence energy transfer may also be used characterize molecules that interfere with the formation of AAC-11 polypeptide dimers, trimers, tetramers or higher order structures, or structures formed by AAC-11 polypeptide bound to another polypeptide. AAC-11 polypeptide can be labeled with both a donor and acceptor fluorophore. Upon mixing of the two labeled species and excitation of the donor fluorophore, fluorescence energy transfer can be detected by observing fluorescence of the acceptor. Compounds that block dimerization will inhibit fluorescence energy transfer.

Surface plasmon resonance can be used to monitor the effect of molecules on AAC-11 polypeptide self-association as well as an association of AAC-11 polypeptide and another polypeptide or molecule. AAC-11 polypeptide can be coupled to a sensor chip at low site density such that covalently bound molecules will be monomeric. Solution protein can then passed over the AAC-11 polypeptide-coated surface and specific binding can be detected in real-time by monitoring the change in resonance angle caused by a change in local refractive index. This technique can be used to characterize the effect of molecules on kinetic rates and equilibrium binding constants for AAC-11 polypeptide self-association as well as an association of AAC-11 polypeptide and another polypeptide or molecule.

A scintillation proximity assay may be used to characterize the interaction between an association of AAC-11 polypeptide with another AAC-11 polypeptide or a different polypeptide. AAC-11 polypeptide can be coupled to a scintillation-filled bead. Addition of radio-labeled AAC-11 polypeptide results in binding where the radioactive source molecule is in close proximity to the scintillation fluid. Thus, signal is emitted upon AAC-11 polypeptide binding and compounds that prevent AAC-11 polypeptide self-association or an association of AAC-11 polypeptide and another polypeptide or molecule will diminish signal.

ICS biosensors have been described by AMBRI (Australian Membrane Biotechnology Research Institute). The, couple the self-association of macromolecules to the closing of gramacidin-facilitated ion channels in suspended membrane bilayers and hence to a measurable change in the admittance (similar to impedance) of the biosensor. This approach is linear over six decades of admittance change and is ideally suited for large scale, high through-put screening of molecule combinatorial libraries.

In other embodiments of the invention there are provided methods for identifying compounds which bind to or otherwise interact with and inhibit or activate an activity or expression of a polypeptide and/or polynucleotide of the invention comprising: contacting a polypeptide and/or polynucleotide of the invention with a compound to be screened under conditions to permit binding to or other interaction between the compound and the polypeptide and/or polynucleotide to assess the binding to or other interaction with the compound, such binding or interaction preferably being associated with a second component capable of providing a detectable signal in response to the binding or interaction of the polypeptide and/or polynucleotide with the compound; and determining whether the compound binds to or otherwise interacts with and activates or inhibits an activity or expression of the polypeptide and/or polynucleotide by detecting the presence or absence of a signal generated from the binding or interaction of the compound with the polypeptide and/or polynucleotide.

Another example of an assay for AAC-11 agonists is a competitive assay that combines AAC-11 and a potential agonist with AAC-11-binding molecules, recombinant AAC-11 binding molecules, natural substrates or ligands, or substrate or ligand mimetics, under appropriate conditions for a competitive inhibition assay. AAC-11 can be labeled, such as by radioactivity or a colorimetric compound, such that the number of AAC-11 molecules bound to a binding molecule or converted to product can be determined accurately to assess the effectiveness of the potential antagonist.

Potential antagonists include, among others, peptides, polypeptides and antibodies that bind to a polynucleotide and/or polypeptide of the invention and thereby inhibit or extinguish its activity or expression. Potential antagonists also may be a peptide, a polypeptide such as a closely related protein or antibody that binds the same sites on a binding molecule, such as a binding molecule, without inducing AAC-11-induced activities, thereby preventing the action or expression of AAC-11 polypeptides and/or polynucleotides by excluding AAC-11 polypeptides and/or polynucleotides from binding. Other potential antagonists include antisense molecules (see Okano, *J. Neurochem.* 56: 560 (1991); *OLIGODEOXYNUCLEOTIDES AS ANTISENSE INHIBITORS OF GENE EXPRESSION*, CRC Press, Boca Raton, Fla. (1988), for a description of these molecules). Preferred potential antagonists include compounds related to and variants of AAC-11.

Other examples of polypeptide antagonists include antibodies or, in some cases, oligonuclcotides or proteins which are closely related to the ligands, substrates, receptors, enrymes, etc., of the polypeptide, which antagonists bind to the polypeptide of the present invention but do not elicit a response, so that the activity, of the polypeptide is prevented.

It will be readily appreciated by the skilled artisan that a polypeptide and/or polynucleotide of the present invention may also be used in a method for the structure-based design of an agonist, antagonist or inhibitor of the polypeptide and/or polynucleotide, by: (a) determining in the first instance the three-dimensional structure of the polypeptide and/or polynucleotide, or complexes thereof (b) deducing the three-dimensional structure for the likely reactive site(s), binding site(s) or motif(s) of an agonist, antagonist or inhibitor: (c) synthesizing candidate compounds that are predicted to bind to or react with the deduced binding site(s), reactive site(s), and/or motif(s): and (d) testing whether the candidate compounds are indeed agonists, antagonists or inhibitors.

It will be further appreciated that this will normally be an iterative process, and this iterative process may be performed using automated and computer-controlled steps.

In a further aspect, the present invention provides methods of treating abnormal conditions such as, for instance, degenerative diseases, cancer, etc., related to either an excess of an under-expression of, an elevated activity of, or a decreased activity of AAC-11 polypeptide and/or polynucleotide.

If the expression and/or activity, of the polypeptide and/or polynucleotide is in excess, several approaches are available. One approach comprises administering to an individual in need thereof an inhibitor compound (antagonist) as herein described, optionally in combination with a pharmaceutically acceptable carrier, in an amount effective to inhibit the function and/or expression of the polypeptide and/or polynucleotide, such as, for example, by blocking the binding of ligands, substrates, receptors, enzymes, etc., or by inhibiting a second signal, and thereby alleviating the abnormal condition. In another approach, soluble forms of the polypeptides still capable of binding the ligand, substrate, enzymes, receptors, etc. in competition with endogenous polypeptide and/or polynucleotide may be administered. Typical examples of such competitors include fragments of the AAC-11 polypeptide and/or polynucleotide.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heaw chain of human IgG, particularly IgGI, where fusion takes place at the hinge region. In a particular embodiment, the FCC part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

In still another approach, expression of the gene encoding endogenous AAC-11 polypeptide can be inhibited using expression blocking techniques. This blocking may be targeted against any step in gene expression, but is preferably targeted against transcription and/or translation. Examples of a known technique of this sort involve the use of antisense sequences, either internally generated or separately administered (see, for example, O'Connor, *J Neutrochem* (1991) 56:560 in Oligodeoxynucleotides as Antisense Inhibitors of Gene Expression, CRC Press, Boca Raton, Fla. (1988)). Alternatively, oligonucleotides which form triple helices with the gene can be supplied (see. for example, Lee et al., *Nucleic Acids Res* (1979) 6:3073; Cooney et al., *Science* (1988) 241:456. Dervan et al., *Science* (1991) 251:1360).

These oligomers can be administered per se or the relevant oligomers can be expressed in vivo.

The antagonists and agonists of the invention may be employed, for instance, to prevent, inhibit and/or treat diseases, including degenerative diseases and cancer.

Compositions and Administration

In a further aspect of the invention there are provided compositions comprising a AAC-11 to polynucleotide and/or a AAC-11 polypeptide for administration to a cell or to a multicellular organism.

The invention also relates to compositions comprising a polynucleotide and/or a polypeptides discussed herein or their agonists or antagonists. The polypeptides and polynucleotides of the invention may be employ,ed in combination with a non-sterile or sterile carrier or carners for use with cells, tissues or organisms, such as a pharmaceutical carrier suitable for administration to an individual. Such compositions comprise, for instance, a media additive or a therapeutically effective amount of a polypeptide and/or polynucleotide of the invention and a pharmaceutically acceptable carrier or excipient. Such carriers may include, but are not limited to, saline, buffered saline, dextrose, water, glyeerol, ethanol and combinations thereof. The formulation should suit the mode of administration.

Polypeptides, polynucleotides and other compounds of the invention may be employed alone or in conjunction with other compounds, such as therapeutic compounds.

In a further aspect, the present invention provides for pharmaceutical compositions comprising a therapeutically effective amount of a polypeptide and/or polynucleotide, such as the soluble form of a polypeptide and/or polynucleotide of the present invention, agonist or antagonist peptide, in combination with a pharmaceutically acceptable carrier or excipient. By "therapeutically effective amount" it is meant a concentration of polypeptide and/or polynucleotide which is capable of affecting the survival rate of cells. Such carriers include, but are not limited to, saline, buffered saline, dextrose, water, glycerol, ethanol, and combinations thereof.

The composition sill be adapted to the route of administration.

In a further aspect, the present invention provides methods of inhibiting apoptosis in cells comprising administering to the cell an effective amount of an AAC-11 polypeptide and/or AAC-11 polynucleotide. By "effective amount" it is meant a concentration of polynucleotide or polypeptide which is capable of increasing the survival rate of cells. Those of skill in the art can routinely determine such amounts in accordance with the teachings provided herein. In a preferred embodiment of the present invention, an AAC-11 polynucleotide, preferably an AAC-11$_{short}$ polynucleotide [SEQ ID NO: 5], is administered to the cells so that the cell encodes an AAC-11 polypeptide which inhibits apoptosis in the cells. The AAC-11 polynucleotides of the present invention may be introduced into the cells using any! well known technique including, but not limited to, infection, transduction, transfection, transvection and transformation. Such techniques are reviewed, for example, in Sambrook et al., *Molecular Cloning, A Laboratory Manual*, 2nd Ed., Cold Spring Harbor Laboratory Press, Cold Spring Harbor, New York, 1989. The polynucleotide sequences can be introduced alone or with other nucleic acid sequences such as those encoding a selectable marker and/or reporter sequence. For example, a nucleic acid sequence of the present invention can be joined to a vector containing a selectable marker. The vector constrict is then introduced into the cell. Selection of appropriate vectors and promoters for expression in a selected cell is a well known procedure and the requisite techniques for constriction of expression vectors, introduction of the vector into the cell and expression in the cell are routine skills in the art.

In a farther aspect, the present invention provides methods of inhibiting apoptosis in cells comprising administering to the cell an effective amount of an AAC-11 polypeptide and/or AAC-11 polynucleotide. By "effective amount" it is meant a concentration of polynucleotide or polypeptide which is capable of increasing the survival rate of cells. Those of skill in the art can routinely determine such amounts in accordance with the teachings provided herein. In a preferred embodiment of the present invention, an AAC-11 polynucleotide, preferably an AAC-11$_{short}$ polynucleotide [SEQ ID NO: 5], is administered to the cells so that the cell encodes an AAC-11 polypeptide which inhibits apoptosis in the cells. The AAC-11 polynucleotides of the present invention may be introduced into the cells using any well knows technique including, but not limited to, infection, transduction, transfection, transvection and transformation. Such techniques are reviewed, for example, in Sambrook et al., *Molecular Cloning, A Laboratory Manual*, 2nd Ed., Cold Spring Harbor Laboratory Press, Cold Spring Harbor, New York. 1989. The polynucleotide sequences can be introduced alone or with other nucleic acid sequences such as those encoding a selectable marker and/or reporter sequence. For example, a nucleic acid sequence of the present invention can be joined to a vector containing a selectable marker. The vector construct is then introduced into the cell. Selection of appropriate vectors and promoters for expression in a selected cell is a well known procedure and the requisite techniques for construction of expression vectors, introduction of the vector into the cell and expression in the cell are routine skills in the art.

In a further aspect, the present invention provides methods of treating degenerative diseases comprising administering to the patient an effective amount of an AAC-11 polypeptide and/or AAC-11 polynucleotide. By "effective amount" it is meant a concentration of polynucleotide or polypeptide which is capable of increasing the survival rate of the cells affected by the degenerative disease. Those of skill in the art can routinely determine such amounts in accordance with the teachings provided herein. In a preferred embodiment of the present invention, an AAC-11 polynucleotide, preferably an AAC-11$_{short}$ polynucleotide [SEQ ID NO: 5], is administered to the affected cells so that they encode an AAC-11 polypeptide which inhibits apoptosis in the affected cells. The AAC-11 polynucleotides of the present invention may be introduced into the affected cells using any well known technique including, but not limited to, infection, transduction, transfection, transvection and transformation. Such techniques are reviewed, for example, in Sambrook ct al., *Molecular Cloning, A Laboratory Maual*, 2nd Ed., Cold Spring Harbor Laboratory Press, Cold Spring Harbor. N.Y., 1989. The polynucleotide sequences can be introduced alone or with other nucleic acid sequences such as those encoding a selectable marker and/or reporter sequence. For example, a nucleic acid sequence of the present invention can be joined to a vector containing a selectable marker. The vector construct is then introduced into the affected cells. Selection of appropriate vectors and promoters for expression in a selected cell is a well known procedure and the requisite techniques for construction of expression vectors, introduction of the vector into the cell and expression in the cell are routine skills in the art.

In a further aspect, the present invention provides methods of inducing apoptosis in cells by inhibiting the expression of AAC-11 polynucleotides and/or the activity of AAC-11 polypeptides. For example, apoptosis in a cell may be induced by administering using well known techniques an effective amount of oligonucleotides which hybridize to a portion of an AAC-11 polynucleotide sequence and which inhibit expression of the AAC-11 polynucleotide sequence. Alternatively, apoptosis in a cell may be induced by administering thereto using well known techniques an effective amount of antibodies against a polypeptide encoded by an AAC-11 polynucleotide and which antibodies bind to the polypeptide, thus inhibiting the activity of the polypeptide. By "effective amount" it is meant a concentration of oligonucleotides or antibodies which is capable of increasing the rate of apoptosis in cells. Drugs which inhibit the activity of an AAC-11 polypeptide can also be used. Drugs capable of inhibiting activity of the polypeptides can be identified routinely based upon increased apoptosis and cell death in host cells containing vectors comprising an AAC-11 polynucleotide sequence of the present invention.

In a further aspect, the present invention provides methods of treating cancer by inhibiting the expression of AAC-11 polynucleotides and/or the activity of AAC-11 polypeptides. For example, apoptosis in cancer cells may be induced by administering, using well known techniques, an effective amount of oligonucleotides which hybridize to a portion of an AAC-11 polynucleotide sequence and which inhibit expression of the AAC-11 polynucleotide sequence. Alternatively, apoptosis in the cancer cells may be induced by administering thereto, using well known techniques, an effective amount of antibodies against a polypeptide encoded by an AAC-11 polynucleotide and which antibodies bind to the poly,peptide, thus inhibiting the activity of the polypeptide. By "effective amount" it is meant a concentration of oligonucleotides or antibodies which is capable of increasing the rate of apoptosis in cells.

Identification

A nucleic acid sequence of the present invention was identified using a functional expression cloning strategy. (See Tewarn et al., Cancer Research. 57. 4063–4069 (1997), which is incorporated by reference herein in its entirety). In these experiments, cDNA was prepared from IGF-I and cycloheximide treated BALB/c3T3 cells and unidirectionally cloned into the expression vector pcDNA3. The cDNA library was screened with a subtracted cDNA probe from IGF-I-stimulated cells. Candidate cDNA clones were then individually transfected into BALB/c3T3 cells, selected in G418 for one to two weeks, and then cultured in serum-free medium containing G4818. In the absence of serum, mock-transfected BALB/c3T3 cells and individual colonies of cells stably transfected with pcDNA3 vector (controls) died completely within 2 weeks of serum deprivation. However, approximately 20–50 colonies /$10^6$ cells transfected with the murine cDNA library survived after 6 weeks in sertim-free medium. In one of these colonies, a 1023-bp cDNA was recovered by PCR and is referred to herein as AAC-11 (antiapoptosis clone 11).

The original cDNA library, was rescreened with an AAC-11 cDNA probe to identify, potential AAC-11 isofonns. In addition to isolating the identical AAC-11 cDNA identified by the PCR approach. a 3714-bp cDNA was isolated and is referred to herein as AAC-11$_{long}$ [SEQ ID NO:1]. The longer cDNA contains an additional 850 bp in the 5' end of the original AAC-11 cDNA (referred to herein as AAC-11$_{short}$ [SEQ ID NO:5]) and 1865 bp in the 3' end that replace the polyadenylic acid tail of AAC-11$_{short}$. A separate 3' polyadenylic acid tail is present in AAC-11$_{long}$, preceded by several AAUAAA polyadenylation signals.

Figure 1A:
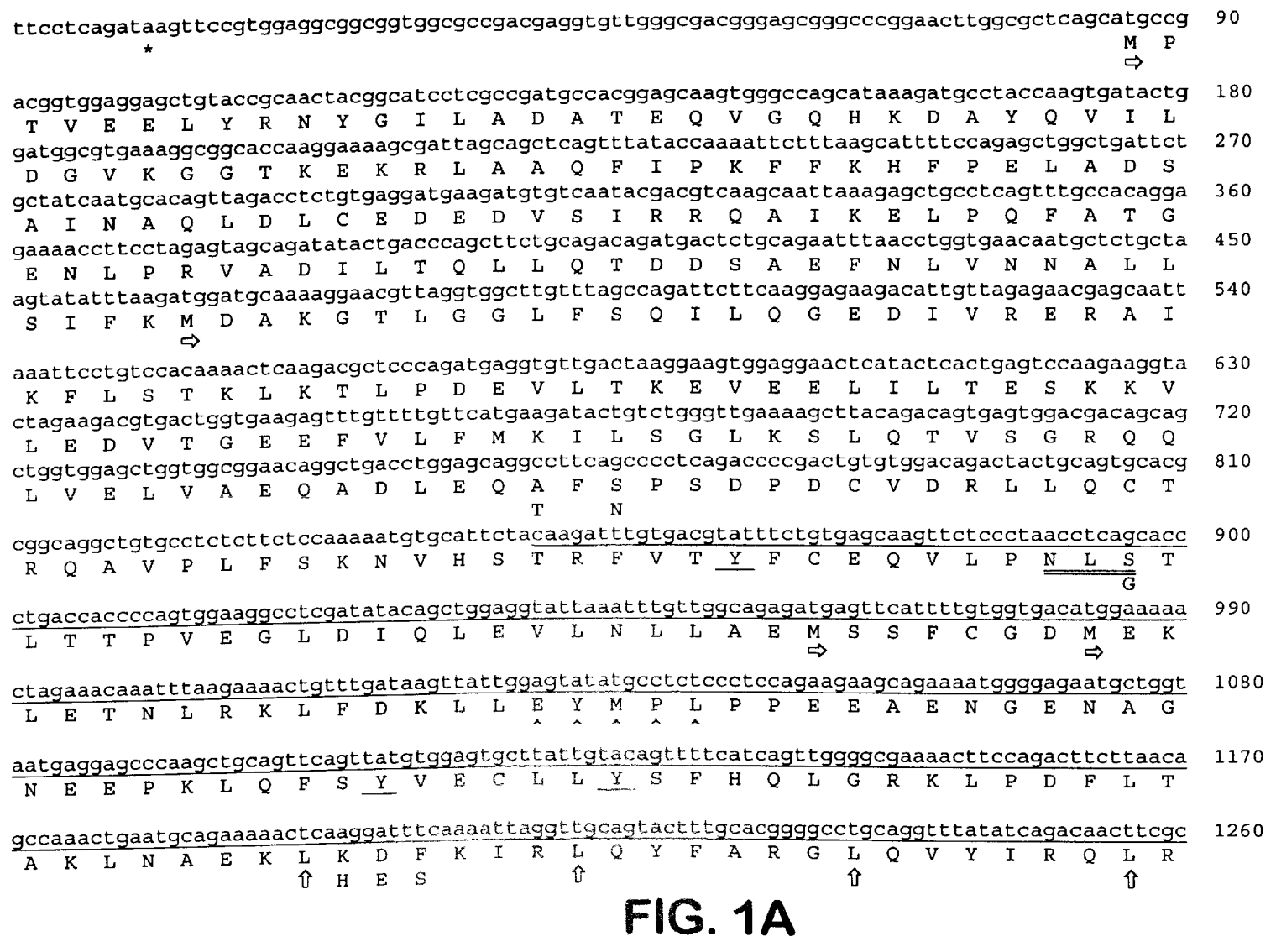

The cDNA and deduced amino acid sequences of both AAC-11 species are shown in FIG. 1. The longest open reading frame (ORF) of AAC-11$_{long}$ contains 1583 bp with several potential methionine initiation sites. In vitro transcription and translation of the AAC-11$_{long}$ cDNA in rabbit reticular lysates yielded a single product of approximately 60 kDa which corresponded to an ORF initiated at the first methionine and codes for 504 amino acids. A second methionine is located in a strong Kozak consensus sequence (Kozak, M. J. Biol. Chem. 1991, 266:19867–19870) with an adenine at position −3 and a glycine at position +4, which should initiate an ORF coding for a protein of approximately 45 kDa. However, a corresponding protein was not translated in vitro.

The cDNA for AAC-11$_{short}$ begins at nucleotide 851 of AAC-11$_{long}$. It has two potential methionine start sites with a consensus Kozak initiation site at the second methionine. The coding region using this methioninie predicts a protein of approximately 25 kDa corresponding to a slightly slower migrating in vitro-translated product (approximately 29 kDa). AAC-11$_{short}$ cDNA ends with a polyadenylic acid tail (14 alanines) at bp 1860 in place of 3 ' noncoding sequences of AAC-11$_{long}$.

Search of NIH GenBank using BLAST and FASTA programs identified several uncharacterized homologous human and rat nucleotide sequences corresponding to the 3' noncoding region (bp 1698–159) of mouse AAC-11$_{long}$ (accession numbers 03004 and H34636; N27512). No other significant nucleotide or protein homologies were identified. An EYMPL amino acid sequence is also present in human and yeast protein phosphatase 2A (accession numbers B34541 and Z34955) and Polyoma virus 61-kDa tumor antigen (accession number M31786). A hydrophobicity plot of the deduced protein sequence of AAC-11$_{long}$ contains no predicted hydrophobic spanning area. A potential protein kinase C phosphorylation site and several potential tyrosine kinase phosphorylation sites are present in the COOH-terminal region encompassed by AAC-11$_{short}$. There are two potential N-linked glycosylation sites. AAC-11 is leucine-rich, particularly in the AAC-11$_{short}$ region (about 12%). A leucine repeat with a lysine in the fifth position is present in the COOH-terminal end. Intervening hydrophobic amino acids are present in the −3 positions before positions 1, 3, 4, and 5, but the overall structure is only weakly consistent with a leucine zipper motif. A basic DNA-binding domain characteristic of the leucine zipper class of transcriptional activators is not present upstream of the leucine repeat.

Experiments performed to examine species homology showed that human AAC-11 cDNA exhibited greater than 90% homologen with the mouse species. Further, the predicted amino acid sequence of human AAC-11 shown in FIG. 1 shows strong homology with mouse AAC-11$_{long}$, with retention of the leucine zipper motif.

Northern blot analysis of mouse tissues probed with a AAC-11$_{short}$ probe demonstrated that the dominant transcript of approximately 4 kb was present in all tissues examined, as well as weaker bands at 3 and 2 kb. In addition, a transcript of approximately 7 kb was present in heart and skeletal muscle, as well as a faint 1.3 kb transcript in skeletal muscle. The Northern blot was also probed with a PCR-generated probe corresponding to the 5' end of the longest ORF of AAC-11$_{long}$ cDNA. This probe did not hybridize to the 3 or 7 kb bands. Additionally, a band of approximately 1 kb was identified in testis. Primer extension of mRNA commencing at nucleotides 1000–1015 gave rise to extended products of about 0.35 and 1 kb corresponding to the short and long forms of AAC-11, respectively.

An AAC-11 mRNA has also been found to be expressed during fetal and postnatal development. A 4 kb AAC-11 transcript was detected in multiple tissues from day 15 and 21 rat embryos and postnatal day 4 including heart, lung, liver, intestines, kidney, and muscle. Several human tumor cell lines also express AAC-11 mRNA including carcinomas of lung, stomach, colon, and nasopharynx as well as HeLa cells and Jurkat T cells. Genomic DNA Southern blotting revealed strong AAC-11 gene conservation in all species examined.

Rabbit polyclonal anti-AAC-11 serum was raised by immunization with a synthetic peptide corresponding to the predicted COOH terminus common to the short and long forms of AAC-11 cDNA. Anti-AAC-11 antibodies were inimunoreactive toward in vilro-translated AAC-11 long and short proteins. Antibody specificity was demonstrated by markedly reduced band intensity using serum that was preabsorbed with the immunogenic peptide. Immunoblotting of BALB/c3T3 lysates revealed a major 55 kDa protein. Detectable minor 22 and 25 kDa proteins were present. The 25 kDa protein was overexpressed in cells transfected with AAC-$11_{short}$ cDNA.

Figure 3:
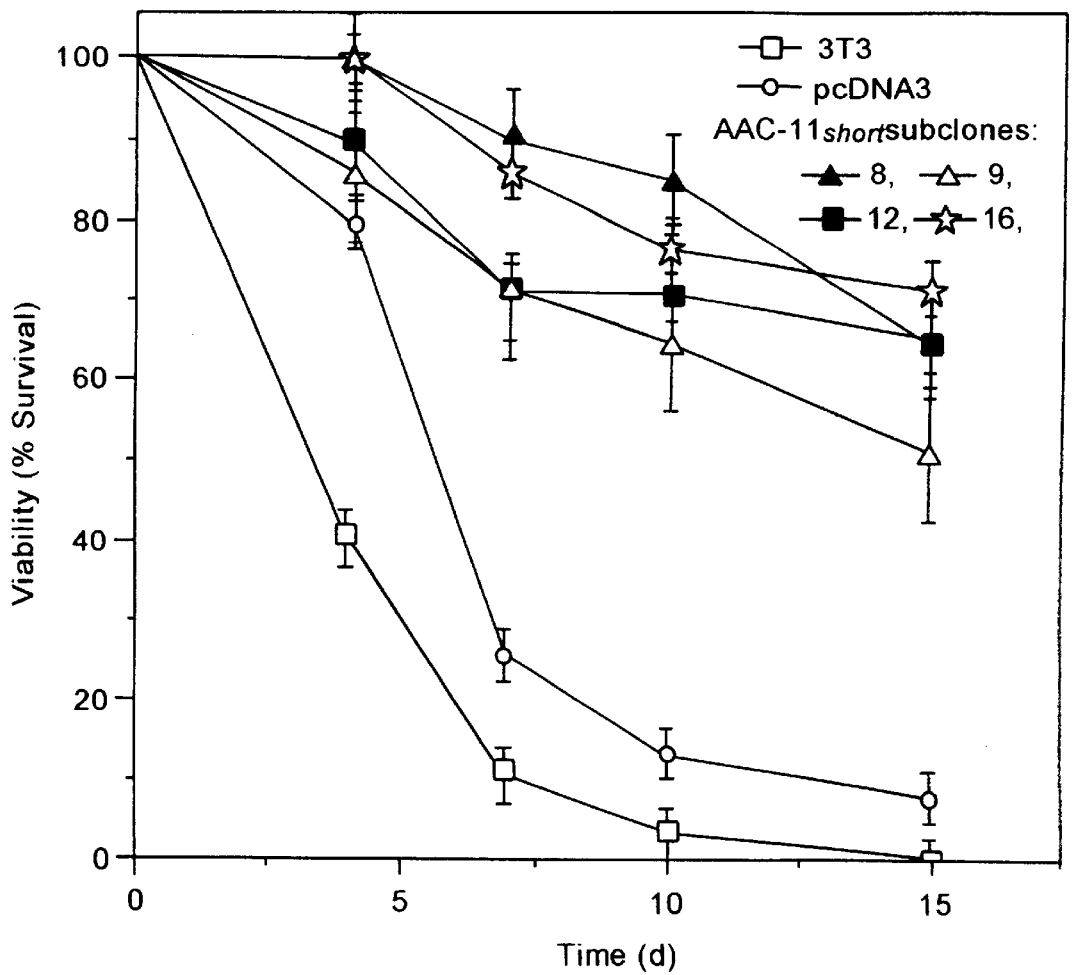
FIG. 3 is a graph showing the time course of wild-type BALB/c3T3 cell death in a serum-free medium as the number of viable cells expressed as a percentage of the cells before the removal of serum as a function of time and represent the mean±SE of triplicate determinations from one of at least three experiments, wherein the cells have been transfected with AAC-11$_{short}$ subclones.
Figure 4:
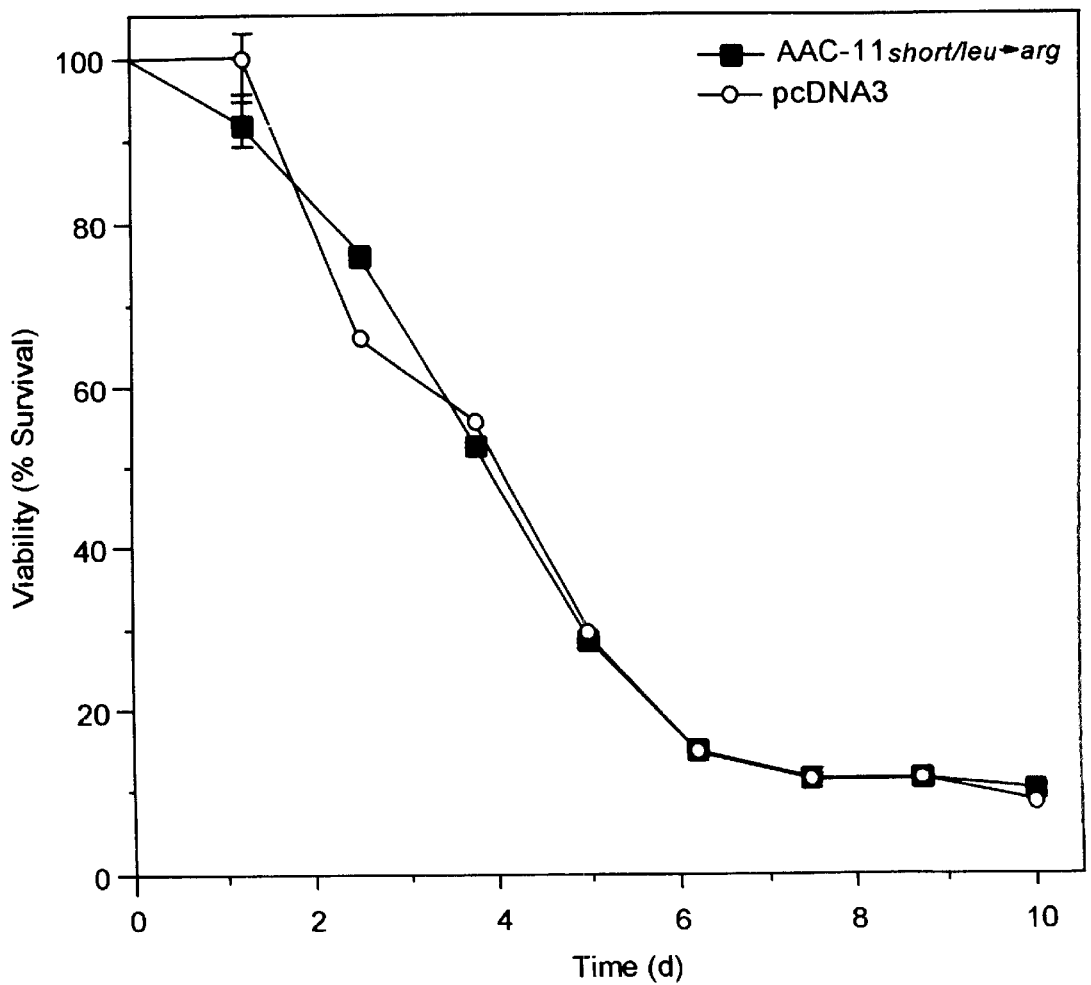
FIG. 4 is a graph showing the time course of wild-type BALB/c3T3 cell death in a serum-free medium as the number of viable cells expressed as a percentage of the cells before the removal of serum as a function of time and represent the mean±SE of triplicate determinations from one of at least three experiments, wherein the cells have been transfected with AAC-11$_{short/Leu-Arg}$.
Figure 5:
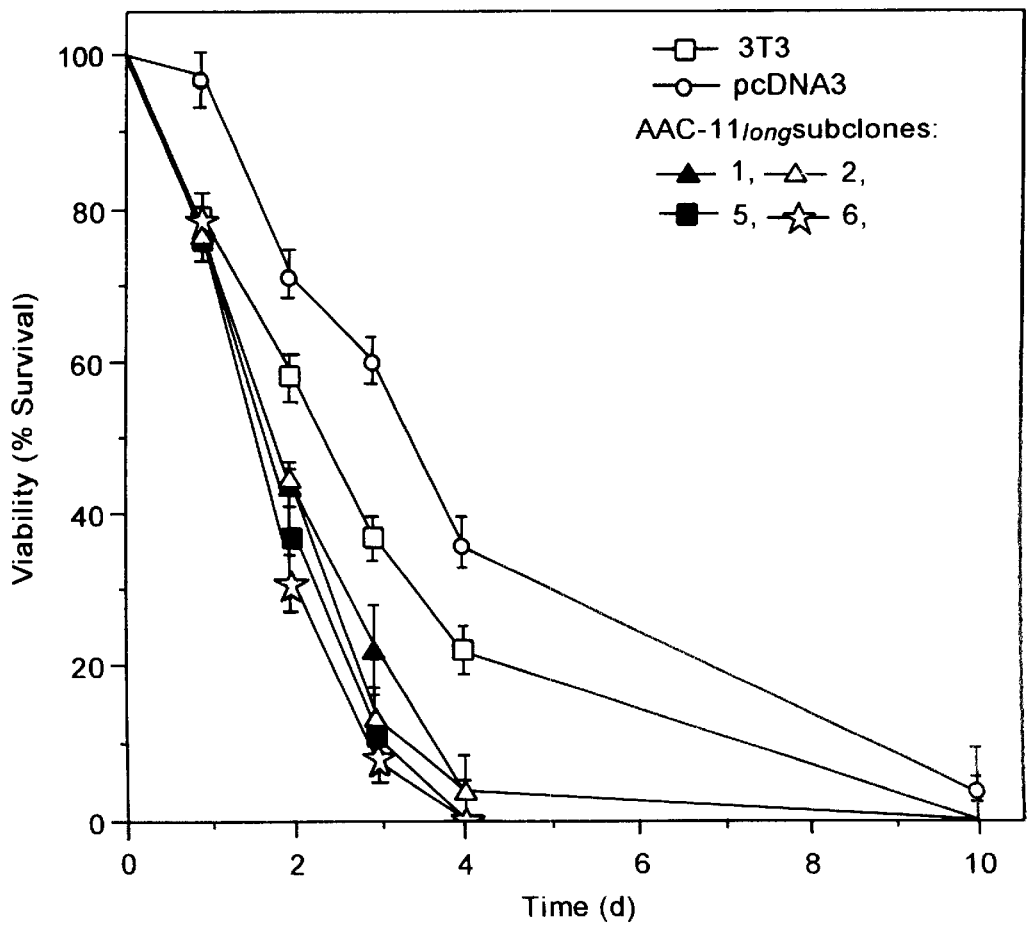
FIG. 5 is a graph showing the time course of wild-type BALB/c3T3 cell death in a serum-free medium as the number of viable cells expressed as a percentage of the cells before the removal of serum as a function of time and represent the mean±SE of triplicate determinations from one of at least three experiments, wherein the cells have been transfected with AAC-11$_{long}$ subclones.

Once the identities of the AAC-11 cDNA and the encoded polypeptides were defined, studies were performed to examine the biological activity of the encoded polypeptides. Transfection with AAC-11 cDNA offered a significant survival advantage to the cells. (See FIGS. 2–5). The time course of wild-type BALB/c3T3 cell death in serum-free medium varied with different cell batches, but over 95% of cell death uniformly occurred by 10 days. (See FIG. 2). Dying cells showed features typical of apoptosis, including membrane blebbing chromatin condensation, and ultimately cytoplasmic compaction. Cells transfected with pcDNA3 vector had a slight survival advantage, but near-complete loss of viability, generally occurred by day 12. In contrast, over 40% of cells transfected with pooled AAC-$11_{short}$ transfectants (see FIG. 2) and individually tested AAC-$11_{short}$ subclones (see FIG. 3) were still viable at 15–30 days. Viable AAC-$11_{short}$ transfectants persisted for up to 4 months in the absence of serum and regrew to confluence on the addition of serum.

Survival of cells transfected with the expression plasmid pcDNA3 encoding the antiapoptotic protein bcl-2 displayed intermediate survival was also determined. Approximately 50% of cells transfected with bcl-2 remained viable at 12 days, but there was no survival at 4 weeks. Proliferating or quiescent AAC-$11_{short}$ transfectants were morphologically indistinguishable from wild-type cells, exhibited a similar doubling time remained contact-inhibited and did not proliferate in serum-free medium. To assess the functional contribution of the putative leucine zipper motif, the two leucines preceding the terminal lysine were mutated to arginines. This mutated clone is referred to herein as AAC-$11_{short/Leu-Arg}$. AAC-$11_{short/Leu-Arg}$ provided no protection against serum deprivation. (See FIG. 3). Further, in contrast to the profound protective effect of AAC-$11_{short}$, transfection with AAC-$11_{long}$ cDNA conferred no resistance to apoptosis. In fact, the rate of cell death in the first few days after serum removal in cells transfected with AAC-$11_{long}$ increased by up to 50% compared to that of vector controls. (See FIG. 5).

It is believed that the AAC-$11_{short}$ proteins and polypeptides with similar anti-apoptotic activity are important regulators of the cell death pathway that affects development, tissue regeneration, degenerative diseases, and cancer. Accordingly, the polynucleotide sequences, polypeptides encoded thereby and methods of the present invention are not only useful in studying the mechanism of apoptosis in cells, but may also be useful in modulating the cell death pathway in degenerative diseases and in cancer.

Glossary

The following definitions are provided to facilitate understanding of certain terms used frequently herein.

"Host cell" is a cell which has been transformed or transfected, or is capable of transformation or transfection by an exogenous polynucleotide sequence.

"Identity," as known in the art, is a relationship between two or more polypeptide sequences or two or more polynucleotide sequences, as determined by, comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk. A. M., ed., Oxford University Press, New York, 1988; *Biocomputing: Informatics and Genomne Projects*, Smith, D. W., ed., Academic Press, New York, 1993; *Computer Analyxix of Sequence Data*, Part I. Griffin, A. M., and Griffin, H. G., eds. Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press. New York, 1991; and Carillo, H., and Lipman, D., SIAM *J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devercux, J., et al., *Nucleic Acids Research* 12(1): 387 (1984)), BLASTP, BLASTN, and FASTA (Atschul, S. F. et al., *J. Molec. Biol.* 215: 403–410 (1990). The BLAST X program is publicly available from NCBI and other sources (*BLAST Manual, Altschul*, S., et al., NCBI NLM NIH Bethesda, Md. 20894; Altschul, S., et al., *J. Mol. Biol.* 215: 403–410 (1990). The well known Smith Waterman algorithm may also be used to determine identity.

Parameters for polypeptide sequence comparison include the following: Algorithm: Needleman and Wunsch, J. Mol Biol. 48: 443–453 (1970)

Comparison matrix: BLOSSUM62 from Hentikoff and Hentikoff, Proc. Natl. Acad. Sci. USA. 89:10915–10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following: Algorithm: Needleman and Wunsch. J. Mol Biol. 48: 443–453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid comparisons.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 50, 60, 70, 80, 85, 90, 95, 97 or 100% identity to the reference sequence of SEQ ID NO:1, wherein said polynucleotide sequence may be identical to the reference sequence of SEQ ID NO:1, or may include up to a certain integer number of nucleotide alterations as compared to the reference sequence, wherein said alterations are selected from the group consisting of at least one nucleotide deletion, substitution including transition and transversion, or insertion, and wherein said alterations may occur at the 5' or 3' terminal positions of the reference nucleotide sequence or anywhere between those terminal positions interspersed either individually among the nucleotides in the reference sequence or in one or more contiguous groups within the reference sequence, and wherein said number of nucleotide alterations is determined by multiplying the total number of nucleotides in SEQ ID NO:1 by the integer defining the percent identity divided by 100 and then subtracting that product from said total number of nucleotides in SEQ ID NO:1, or:

$$n_n \leq x_n - (x_n \bullet y),$$

wherein $n_n$ is the number of nucleotide alterations, $x_n$ is the total number of nucleotides in SEQ ID NO:1, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and • is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

By way of example, a polynucleotide sequence of the present invention may be identical to the reference sequence of SEQ ID NO:1, that is it may be 100% identical, or it may include up to a certain integer number of nucleic acid alterations as compared to the reference sequence such that the percent identity is less than 100% identity. Such alterations arc selected from the group consisting of at least one nucleic acid deletion substitution, including transition and transversion, or insertion, and wherein said alterations may occur at the 5' or 3' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of nucleic acids in SEQ ID NO:1 by the integer defining the percent identity divided by 100 and then subtracting that product from said total number of nucleic acids in SEQ ID NO:1, or:

$$n_n \leq x_n - (x_n \bullet y),$$

wherein $n_n$ is the number of nucleic acid alterations $x_n$ is the total number of nucleic acids in SEQ ID NO:1 y is, for instance 0.70 for 70%, 0.80 for 80%, 0.85 for 85% etc., • is the symbol for the multiplication operator, and wherein any non-integer product of $x_n$ and y is rounded dozen to the nearest integer prior to subtracting it from $x_n$.

(2) Polypeptide embodiments further include an isolated polypeptide comprising a polypeptide having at least a 50, 60, 70, 80, 85, 90, 95, 97 or 100% identity to a polypeptide reference sequence of SEQ ID NO:2, wherein said polypeptide sequence may be identical to the reference sequence of SEQ ID NO:2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \bullet y),$$

wherein $n_a$ is the number of amino acid alterations, $x_a$ is the total number of amino acids in SEQ ID NO:2, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and • is the symbol for the multiplication operator, and wherein any non-integer product of $x_a$ and y is rounded down to the nearest integer prior to subtracting it from $x_a$.

By way of example, a polypeptide sequence of the present invention may be identical to the reference sequence of SEQ ID NO:2, that is it may be 100% identical or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \bullet y),$$

wherein $n_a$ is the number of amino acid alterations, $x_a$ is the total number of amino acids in SEQ ID NO:2, y is, for instance 0.70 for 70%, 0.80 for 80%, 0.85 for 85% etc., and • is the symbol for the multiplication operator, and wherein any non-integer product of $x_a$ and y is rounded down to the nearest integer prior to subtracting it from $x_a$.

As an illustration, by a polynucleotide having a nucleotide sequence having at least, for example 95% "identity" to a reference nucleotide sequence of SEQ ID NO:1 it is intended that the nucleotide sequence of the polynucleotide is identical to the reference sequence except that the polynucleotide sequence may include up to five point mutations per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may, be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO:2. In other words to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

"Isolated" means altered "by the hand of man" from its natural state. i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein.

"Polynucleotide(s)" generally refers to any polyribonucleotide or polydeoxribonucleotide which may be unmodified RNA or DNA or modified RNA or DNA. "Polynucleotide(s)" include, without limitation single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzmatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same tope of modification may, be present in the same or varying degree at several sites in a given polypeptide. Also, a given polypeptide may contain many types of modifications. Modifications can occur anywhere in a polypeptide, including the peptide backbone, the amino acid side-chains and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cynclization, disulfide bond formation, demethylation, formation of covalent cross-links, formation of cysteine, formation of pytoglutamate, formylation, ganra-carboxylation, gly,cosylation, GPI anchor formation, hydroxylation, Iodination, methylation, myristoylation, oxidation, proteolytic processing, phosphorylation, prenylation, racemization., glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *PROTEIINS—STRUCTURE AND MOLEACULAR PROPERTIES*, 2nd Ed., T. E. Creighton, W. H. Freeman and Company, New York (1993) and Wold, F., Posttranslational Protein Modifications: Perspectives and Prospects, pgs. 1–12 in *POSTTRANSLATONAL COVALENT MODIFICATION OF PROTEINS*, B. C. Johnson, Ed., Academic Press, New York (1983); Seifter et al., *Meth. Enzymol.* 182:626–646 (1990) and Rattan et al., *Protein Synthesis: Posttranslational Modificatons and Aging*, Ann. N.Y. Acad. Sci. 663: 48–62 (1992). Polypeptides may be branched or cyclic, with or without branching. Cyclic, branched and branched circular polypeptides may result from posttranslational natural processes and may be made by entirely synthetic methods, as well.

"Variant(s)" as the tenn is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

EXAMPLES

Example 1

Cell Lines

BALB/c3T3 cells were obtained from American Type Culture Collection and passaged in DMEM containing 5% fetal bovine serum (FBS) and 5% calf serum.

Example 2 cDNA Library Preparation and Screening

To potentially enrich cells with mRNAs for survival proteins, BALB/c3T3 cells were maintained in 0.5% FBS for 48 hours and then treated for 3 hours with cycloheximide (10 $\mu$g/ml, Sigma Chemical Co., St. Louis, Mo.) and insulin-like growth factor I (50 ng/ml), a growth factor reported to enhance fibroblast survival by Rubin, R. and Baserga, R. *Lab. Invest.* 1995, 73:311–331. RNA was prepared by guanidinium thiocyanate lysis and centrifugation through a CsCl cushion as described by Chirgwin et al. *Biochemistry* 1979, 18:5294–5299. An oligodeoxythymidylic acid-primed cDNA library was prepared by CLONTECH Laboratories, Inc. (Palo Alto, Calif.). cDNA was unidirectionally cloned into the multiple cloning site of pcDNA3 expression vector using 5' NotI and 3' BstI linkers. Aliquots (50 $\mu$g) of the cDNA library, or pcDNA3 vector were transfected into $10^6$ BALB/c3T3 cells using the calcium phosphate precipitation method described by Shen et al. *Mol. Cell Biol.* 1982, 2:1145–1154 and the Promega transfection kit (Promega Corp., Madison, Wis.). Three days after transfection, G418 (1 mg/ml) was added to obtain stable transfectants. After 2 weeks of G418 selection, cell colonies were maintained for 6 weeks in serum-free medium with 0.1% BSA, 50 $\mu$M FeSO$_4$, and G418. Cells that survived the double selection process were regrown for 5 days in the presence of 10% FBS and then selected a second time in serum-free medium. Surviving clones were isolated using cloning cylinders and expanded.

The integrated cDNA inserts within pcDNA3 were identified by PCR of genomic DNA using flanking pcDNA3 vector sequences (5'-CTCCGGATCCACTAGTAACGG-3' [SEQ ID NO:10] and 5'-TCTAGATGCATGCTCGAGCG-3' [SEQ ID NO:11]). To isolate genomic DNA, the cells were lysed in 50 mM Tris (pH 8.0). 20 mM EDTA, 1% SDS, and 100 mM NaCl. The lysate was treated with 250 $\mu$g/ml proteinase K and 100 $\mu$g/ml RNase A before ethanol precipitation and chloroform/phenol extraction. The PCR product was used as a probe to rescreen the original cDNA library. The PCR product and the isolated cDNA were sequenced in both directions using an automated facility with the cycle sequencing technique (Applied Biosystems model 373. Foster City, Calif.). Sequences were compared with GenBank sequences using GCG software. Hydropathy plots were generated using the PenPlot program in GCG.

Example 3

Isolation of Human cDNA

A human gingival cDNA phage library (Tewari et al. *Biochim. Biophys. Acta* 1994, 1209:293–295) was screened with murine AAC-11 cDNA using standard techniques. Human AAC-11 cDNA was rescued within pBluescript with Helper phage R408 (Stratagene. La Jolla, Calif.) and sequenced. The isolated cDNA lacked 1.2 kb of 5' sequences. Thus, the cDNA was used as a probe to screen a human leukemia 5'-stretch plus cDNA library, (CLONTECH Laboratories, Inc., Palo Alto, Calif.) to obtain a full-length cDNA.

Example 4

Plasmid Transfections and Survival Assays

To test the effect of individual cDNAs on survival, BALB/c3T3 cells were transfected with plasmids by the calcium phosphate precipitation technique. G418 (1 mg/ml: Sigma Chemical Co.) was added after 72 hours. Stable transfectants were obtained after 2 weeks and expanded. Cells ($8 \times 10^4$) were plated in 6-well plates overnight. On the indicated days, the plates were washed with HBSS, the attached cells were trypsinized, and their viability was determined by trypan blue exclusion and counting in a hemocytometer.

Example 5

In ritro Translations

In vitro translations were performed using [$^{35}$S] methionine and the Promega TNT rabbit reticular lysate system according to the manufacturer's specifications (Promega Corp. Madison, Wis.). Translated products were visualized by SDS gel electrophoresis and autoradiography.

Example 6

Plasmid Construction

AAC-11$_{short/Leu-Arg}$ cDNA was created bN a two-step PCR procedure. In the first step, a 5' PCR fragment was generated with a primer corresponding to bp 958–975 tailed with a BamHI site (primer A) and a mutagenic primer for leucine$_{(bp\ 1234-1236)}$-arginine (primer B). A 3' PCR fragment was generated in a similar manner for bp 1585–1600 (primer C) and mutagenic primer for leucine$_{(bp\ 1255-1257)}$-arginine (primer D). The PCR fragments were then used as primers in the second PCR step to generate AAC-11$_{short/Leu-Arg}$ cDNA which was digested with BamHI and subcloned into the BamHI site of pcDNA3. The mutated leucines and orientation were confirmed by sequencing. Primer sequences were as follows:

A, 5'-GC<u>GGATCC</u>GAGATGAGTTCATTTCGT-3' [SEQ ID NO:12];

B, 5'-TTGTCTGATATAAACCTGCAGGCCCCTG-3' [SEQ ID NO:13];

C, 5'-GC<u>GGATCC</u>CTATTTCCCCTGAAG-3' [SEQ ID NO:14]; and

D, 5'-CAGGTTTATATCAGACAACTTCGCTTGGCTCT-3' [SEQ ID NO:15]. BamHI sites are underlined: Leu-Arg mutations are shown in bold.

Example 7

RNA Extractions and Northern Blot Analysis

Total cellular RNA from rat embryonic and postnatal tissue was isolated as described by McHugh et al. *Dev. Biol.* 1991, 148:442–458). Tumor cell RNA was isolated as described by Chirgwin et al. *Biochemistry* 1979, 18:5294–5299. A mouse multiple-tissue Northern blot and a eukaryotic genomic DNA Southern blot were obtained from CLONTECH and hybridized with $^{32}$P-labeled random-primed cDNA probes according to standard procedures described by Thomas, P. S. *Methlods Enzymol.* 1983, 100:255–266). PCR-generated cDNA probes for AAC-11$_{long}$ were generated using forward primer 5'-TGGCGCCGACGAGGT-3' [SEQ ID NO:16] and reverse primer 5'-AGCATTGTTCACCAG-3' [SEQ ID NO:17].

Example 8

Generation of Anti-AAC-11 Antibodies and Western Immunoblot

A polyclonal rabbit immune senim was raised by subcutaneous injection of a synthetic 15-mer synthetic peptide (CNLSNFNYERSLQGK) [SEQ ID NO:181]. For immunoblot analysis cell lysates were prepared by suspending pelleted cells in 130 μl of lysis buffer [50 mM Tris (pH 7.9), 5 mM EDTA 250 mM NaCl, 50 mM NaF. 0,1% Triton X-100, 0.1 mM Na$_3$VO$_4$ 0.5 mM phenylmethylsulfonyl fluoride, and 10 μtg/ml each of leupeptin, aprotinin and pepstatin]. Protein (100 μg) was nin on a 10% denaturing SDS-polyacrylamide gel, and transferred to a polyvinylidene difluoride membrane (Millipore Corp., Bedford, Mass.) in buffer containing 10 mM CAPS (3-cyclohexylamino-1-propane sulfonic acid pH 11) and 20% methanol. Membranes were blocked in 5% milk TBS-T buffer [2 mM Tris (pH 7.6), 13.7 mM NaCl, and 0.1% Tween 20] and then washed in TBS-T buffer. Primary antibody was then incubated with the membrane at a dilution of 1: 1000 in 3% milk for 1 hour and then washed in TBS-T. Rabbit antimouse antibody coupled to horseradish peroxidase (Amersham Corp., Arlington Heights, Ill.) was then incubated with the membrane and washed in TBS-T. The blots were developed using the enhanced chemiluminescence system (DuPont Co. NEN Research Products, Boston, Mass.).

What is claimed is:

1. An isolated polynucleotide segment comprising a nucleic acid sequence or the full complement of the entire length of said nucleic acid sequence, wherein said nucleic acid sequence encodes a polypeptide comprising SEQ ID NO:6.

2. A vector comprising the isolated polynucleotide segment of claim 1.

3. An isolated host cell comprising the vector of claim 2.

4. A process for producing a polypeptide comprising culturing the host cell of claim 3 under conditions sufficient for the production of said polypeptide, wherein the polypeptide comprises SEQ ID NO:6.

5. The isolated polynucleotide segment of claim 1 wherein the isolated polynucleotide encodes a fision polypeptide, wherein the fusion polypeptide comprises SEQ ID NO:6.

6. An isolated polynucleotide segment comprising SEQ ID NO:5.

7. A vector comprising the isolated polynucleotide segment of claim 6.

8. An isolated host cell comprising the vector of claim 7.

9. A process for producing a polypeptide comprising culturing the host cell of claim 8 under conditions sufficient for the production of said polypeptide, wherein the polypeptide comprises SEQ ID NO:6.

10. A process for producing a polypeptide comprising culturing the host cell of claim 8 under conditions sufficient for the production of said polypeptide, wherein the polypeptide comprises SEQ ID NO:7.

11. An isolated polynucleotide segment comprising a nucleic acid sequence or the full complement of the entire length of said nucleic acid sequence, wherein said nucleic acid sequence encodes a polypeptide comprising SEQ ID NO:7.

12. A vector comprising the isolated polynucleotide segment of claim 11.

13. An isolated host cell comprising the vector of claim 12.

14. A process for producing a polypeptide comprising culturing the host cell of claim 13 under conditions sufficient for the production of said polypeptide, wherein the polypeptide comprises SEQ ID NO:7.

15. The isolated polynucleotide segment of claim 11, wherein the isolated polynucleotide encodes a fusion polypeptide, wherein the fusion polypeptide comprises SEQ ID NO:7.

* * * * *

SEQUENCE LISTING

<160> NUMBER OF SEQ ID NOS: 18

<210> SEQ ID NO 1
<211> LENGTH: 3715
<212> TYPE: DNA
<213> ORGANISM: Mus musculus

<400> SEQUENCE: 1

```
attcctcaga taagttccgt ggaggcggcg gtggcgccga cgaggtgttg ggcgacggga      60
gcgggcccgg aacttggcgc tcagcatgcc gacggtggag gagctgtacc gcaactacgg     120
catcctcgcc gatgccacgg agcaagtggg ccagcataaa gatgcctacc aagtgatact     180
ggatggcgtg aaaggcggca ccaaggaaaa gcgattagca gctcagttta taccaaaatt     240
ctttaagcat tttccagagc tggctgattc tgctatcaat gcacagttag acctctgtga     300
ggatgaagat gtgtcaatac gacgtcaagc aattaaagag ctgcctcagt ttgccacagg     360
agaaaacctt cctagagtag cagatatact gacccagctt ctgcagacag atgactctgc     420
agaatttaac ctggtgaaca atgctctgct aagtatattt aagatggatg caaaggaac      480 gttaggtggc ttgtttagcc agattcttca aggagaagac attgttagag aacgagcaat     540
taaattcctg tccacaaaac tcaagacgct cccagatgag gtgttgacta aggaagtgga     600
ggaactcata ctcactgagt ccaagaaggt cctagaagac gtgactggtg aagagtttgt     660
tttgttcatg aagatactgt ctgggttgaa aagcttacag acagtgagtg gacgacagca     720
gctggtggag ctggtggcgg aacaggctga cctggagcag gccttcagcc cctcagaccc     780
cgactgtgtg gacagactac tgcagtgcac gcggcaggct gtgcctctct tctccaaaaa     840
tgtgcattct acaagatttg tgacgtattt ctgtgagcaa gttctcccta acctcagcac     900
cctgaccacc ccagtggaag gcctcgatat acagctggag gtattaaatt tgttggcaga     960
```

```
gatgagttca ttttgtggtg acatggaaaa actagaaaca aatttaagaa aactgtttga  1020
taagttattg gagtatatgc ctctccctcc agaagaagca gaaaatgggg agaatgctgg  1080
taatgaggag cccaagctgc agttcagtta tgtggagtgc ttattgtaca gttttcatca  1140 gttgggggcga aaacttccag acttcttaac agccaaactg aatgcagaaa aactcaagga  1200
tttcaaaatt aggttgcagt actttgcacg gggcctgcag gtttatatca gacaacttcg  1260
cttggctctc cagggtaaaa caggcgaggc cttaaaaaca gaggagaaca agataaaagt  1320
tgttgcactg aaaataacaa acaatatcaa tgttttaatc aaggatctct tccacattcc  1380
tccttcttat aagagcacag taacattgtc ctggaaacct gtgcagaaag ttgagattgg  1440
gcaaaagaga accagtgaag atacaagttc aggttcacca cctaagaagt ctccaggagg  1500
accaaaaaga gatgccagac agatttataa tcctccgagt ggaaagtaca gcagcaatct  1560
gagcaacttt aattatgaga ggagccttca ggggaaatag aggtggccga ggttggggaa  1620
cacgaggaaa tcgaagtcga ggaagactct actgattgtg acgtcacatt cttcagcatt  1680
gtcatgagat taatatactt aaatctacta ctcattggat tgccggggat gtccctttaa  1740
aaggactgct gccttcagct gaaaatgtaa tgttctttct acctttgtat gtatgatcta  1800
cttttgtaaa agaccatggt tgtgtccaag gtaaaaccac aacaatattt ttggatgctt  1860
tgtctgcagc cttgacttgt tttcacaata tcctcactat ccagacttca tcttgtgaat  1920
cttgctttta cacatcttga tggttttttca ctgagatctg actctattgg aaaagtcagt  1980
ctagcctgtg atctggtgaa gatcatcact cttgaaacgt tactgttctc ctccccattc  2040
cgttaggttt ctgcccaaca catggagaag agttaagagc agtcttaacc ttctgctttc  2100
attgttttct aaggaagctg ctaggcagtg ttgtcgcatt cctgccaagt catagaaatg  2160
aagcaccagc ttctcacagt gtacaggcga tgccagcctt ttagaaagaa cttgctttgc  2220
attgcccctt cagtcttctc catattttgg gatacagctt tgaacacagg gtcttattat  2280
ttgaatagga gtacatgtgc ataatatacg tacagacata agcatatgtt gtgtgtgtat  2340
atatgcatgg aacttgagtg tacaaccaat caatacatta aattctcgga aggggtcctc  2400
tgacatagcg attatccctt tgaggctgaa tccattactg acttggtatc taggttttca  2460
ctccagtagg gaggaatttc agtcagctga acttacagat tattattgtt gtttaaaact  2520
aaaaaacaaa ggctgttttt acagagacaa atttaaagac ccttgttggt gaaatacagc  2580
cagatctggt gtacatacag gttcccacag gatctgctat gtaatgttag gatttgggag  2640
acttaaataa ccagggctac cccaagaaat gtgacttggt gacatagtta ccataaaaat  2700
tgctcactcc gcttggcttt tgccactttt caaattttaa cttctcaggt tattaatcag  2760
attattgtgt aagttagcca atagtcttta gattaaggca acagacggga ggttcgtgga  2820
gtgtctcatg ttgggcattt ttagtagccc agactctgtt cttcatttga atgtttcaca  2880 cattttgtt cacagttaat cttccaagtt tactattcaa gtcagaaatt cagatgacat  2940
ttctagtggt ttgctgtttt ggttttttat gtttttggt tttttttgag gtttcatttc  3000
ttacacaggt gttttcatca ccatcaattt tacactgggg gaaaaacaat tcctttgtga  3060
gaatcactgc aagtatttat ggcgaaaata tttttgaaag tttaggtgat acaagtgagc  3120
acaagaagtt ggtcagcttg cctatggagt gctggcaata aactttgaac attccacaag  3180
cctgagctga acctaggctc ccttggaagc tgaacagaca taggaacatg ggattgccag  3240
ctgaatcctg tgaccatta gttatggacc tcagagatag atcagcatgg cctaaagcca  3300
```

-continued

```
tttcaagtac aaaaatgaat tggactatag caacataaat ttgaacacag taacttttcc    3360
tctttgcctg aaggcatttg taaactcggc agaagtaact tgacctcatg tctactgcag    3420
agctcactgc attcacccct cctcatcctt tgcttccttc cccttgccta gtcagtagtt    3480
cataacttag tgttcctttt gcttcagaaa tctgaaagaa aatcttcatg ccatcaatct    3540
ttttcttccg caaggacacc tgtgtctccc ttgtttaaat aaatgtaaat gctcccttat    3600
gcttttgaaa taaatttcct tttgtaaaaa aaaaaaaaa aaaaaaaaa aaaaaaaaa     3660 aaaaaaaaa aaaaaaaaa aaaaaaaaa aaaaaaaaa aaaaaaaaa aaaaa            3715
```

<210> SEQ ID NO 2
<211> LENGTH: 504
<212> TYPE: PRT
<213> ORGANISM: Mus musculus

<400> SEQUENCE: 2

```
Met Pro Thr Val Glu Glu Leu Tyr Arg Asn Tyr Gly Ile Leu Ala Asp
  1               5                  10                  15

Ala Thr Glu Gln Val Gly Gln His Lys Asp Ala Tyr Gln Val Ile Leu
             20                  25                  30

Asp Gly Val Lys Gly Gly Thr Lys Glu Lys Arg Leu Ala Ala Gln Phe
         35                  40                  45

Ile Pro Lys Phe Phe Lys His Phe Pro Glu Leu Ala Asp Ser Ala Ile
     50                  55                  60

Asn Ala Gln Leu Asp Leu Cys Glu Asp Glu Asp Val Ser Ile Arg Arg
 65                  70                  75                  80

Gln Ala Ile Lys Glu Leu Pro Gln Phe Ala Thr Gly Glu Asn Leu Pro
                 85                  90                  95

Arg Val Ala Asp Ile Leu Thr Gln Leu Leu Gln Thr Asp Asp Ser Ala
            100                 105                 110

Glu Phe Asn Leu Val Asn Asn Ala Leu Leu Ser Ile Phe Lys Met Asp
        115                 120                 125

Ala Lys Gly Thr Leu Gly Gly Leu Phe Ser Gln Ile Leu Gln Gly Glu
    130                 135                 140

Asp Ile Val Arg Glu Arg Ala Ile Lys Phe Leu Ser Thr Lys Leu Lys
145                 150                 155                 160

Thr Leu Pro Asp Glu Val Leu Thr Lys Glu Val Glu Leu Ile Leu
                165                 170                 175

Thr Glu Ser Lys Lys Val Leu Glu Asp Val Thr Gly Glu Glu Phe Val
            180                 185                 190

Leu Phe Met Lys Ile Leu Ser Gly Leu Lys Ser Leu Gln Thr Val Ser
        195                 200                 205

Gly Arg Gln Gln Leu Val Glu Leu Val Ala Glu Gln Ala Asp Leu Glu
    210                 215                 220

Gln Ala Phe Ser Pro Ser Asp Pro Asp Cys Val Asp Arg Leu Leu Gln
225                 230                 235                 240

Cys Thr Arg Gln Ala Val Pro Leu Phe Ser Lys Asn Val His Ser Thr
                245                 250                 255

Arg Phe Val Thr Tyr Phe Cys Glu Gln Val Leu Pro Asn Leu Ser Thr
            260                 265                 270

Leu Thr Thr Pro Val Glu Gly Leu Asp Ile Gln Leu Glu Val Leu Asn
        275                 280                 285

Leu Leu Ala Glu Met Ser Ser Phe Cys Gly Asp Met Glu Lys Leu Glu
    290                 295                 300
```

-continued

Thr Asn Leu Arg Lys Leu Phe Asp Lys Leu Leu Glu Tyr Met Pro Leu
305                 310                 315                 320

Pro Pro Glu Glu Ala Glu Asn Gly Glu Asn Ala Gly Asn Glu Pro
            325                 330                 335

Lys Leu Gln Phe Ser Tyr Val Glu Cys Leu Leu Tyr Ser Phe His Gln
                340                 345                 350

Leu Gly Arg Lys Leu Pro Asp Phe Leu Thr Ala Lys Leu Asn Ala Glu
            355                 360                 365

Lys Leu Lys Asp Phe Lys Ile Arg Leu Gln Tyr Phe Ala Arg Gly Leu
370                 375                 380

Gln Val Tyr Ile Arg Gln Leu Arg Leu Ala Leu Gln Gly Lys Thr Gly
385                 390                 395                 400

Glu Ala Leu Lys Thr Glu Glu Asn Lys Ile Lys Val Val Ala Leu Lys
                405                 410                 415

Ile Thr Asn Asn Ile Asn Val Leu Ile Lys Asp Leu Phe His Ile Pro
                420                 425                 430

Pro Ser Tyr Lys Ser Thr Val Thr Leu Ser Trp Lys Pro Val Gln Lys
            435                 440                 445

Val Glu Ile Gly Gln Lys Arg Thr Ser Glu Asp Thr Ser Ser Gly Ser
450                 455                 460

Pro Pro Lys Lys Ser Pro Gly Gly Pro Lys Arg Asp Ala Arg Gln Ile
465                 470                 475                 480

Tyr Asn Pro Pro Ser Gly Lys Tyr Ser Ser Asn Leu Ser Asn Phe Asn
                485                 490                 495

Tyr Glu Arg Ser Leu Gln Gly Lys
                500

<210> SEQ ID NO 3
<211> LENGTH: 378
<212> TYPE: PRT
<213> ORGANISM: Mus musculus

<400> SEQUENCE: 3

Met Asp Ala Lys Gly Thr Leu Gly Gly Leu Phe Ser Gln Ile Leu Gln
1               5                   10                  15

Gly Glu Asp Ile Val Arg Glu Arg Ala Ile Lys Phe Leu Ser Thr Lys
            20                  25                  30

Leu Lys Thr Leu Pro Asp Glu Val Leu Thr Lys Glu Val Glu Glu Leu
        35                  40                  45

Ile Leu Thr Glu Ser Lys Lys Val Leu Glu Asp Val Thr Gly Glu Glu
    50                  55                  60

Phe Val Leu Phe Met Lys Ile Leu Ser Gly Leu Lys Ser Leu Gln Thr
65                  70                  75                  80

Val Ser Gly Arg Gln Gln Leu Val Glu Leu Val Ala Glu Gln Ala Asp
                85                  90                  95

Leu Glu Gln Ala Phe Ser Pro Ser Asp Pro Asp Cys Val Asp Arg Leu
            100                 105                 110

Leu Gln Cys Thr Arg Gln Ala Val Pro Leu Phe Ser Lys Asn Val His
        115                 120                 125

Ser Thr Arg Phe Val Thr Tyr Phe Cys Glu Gln Val Leu Pro Asn Leu
130                 135                 140

Ser Thr Leu Thr Thr Pro Val Glu Gly Leu Asp Ile Gln Leu Glu Val
145                 150                 155                 160

Leu Asn Leu Leu Ala Glu Met Ser Ser Phe Cys Gly Asp Met Glu Lys
                165                 170                 175

-continued

```
Leu Glu Thr Asn Leu Arg Lys Leu Phe Asp Lys Leu Leu Glu Tyr Met
            180                 185                 190

Pro Leu Pro Pro Glu Glu Ala Glu Asn Gly Glu Asn Ala Gly Asn Glu
            195                 200                 205

Glu Pro Lys Leu Gln Phe Ser Tyr Val Glu Cys Leu Leu Tyr Ser Phe
            210                 215                 220

His Gln Leu Gly Arg Lys Leu Pro Asp Phe Leu Thr Ala Lys Leu Asn
225                 230                 235                 240

Ala Glu Lys Leu Lys Asp Phe Lys Ile Arg Leu Gln Tyr Phe Ala Arg
            245                 250                 255

Gly Leu Gln Val Tyr Ile Arg Gln Leu Arg Leu Ala Leu Gln Gly Lys
            260                 265                 270

Thr Gly Glu Ala Leu Lys Thr Glu Glu Asn Lys Ile Lys Val Val Ala
            275                 280                 285

Leu Lys Ile Thr Asn Asn Ile Asn Val Leu Ile Lys Asp Leu Phe His
            290                 295                 300

Ile Pro Pro Ser Tyr Lys Ser Thr Val Thr Leu Ser Trp Lys Pro Val
305                 310                 315                 320

Gln Lys Val Glu Ile Gly Gln Lys Arg Thr Ser Glu Asp Thr Ser Ser
            325                 330                 335

Gly Ser Pro Pro Lys Lys Ser Pro Gly Pro Lys Arg Asp Ala Arg
            340                 345                 350

Gln Ile Tyr Asn Pro Pro Ser Gly Lys Tyr Ser Ser Asn Leu Ser Asn
            355                 360                 365

Phe Asn Tyr Glu Arg Ser Leu Gln Gly Lys
            370                 375

<210> SEQ ID NO 4
<211> LENGTH: 504
<212> TYPE: PRT
<213> ORGANISM: Homo sapiens

<400> SEQUENCE: 4

Met Pro Thr Val Glu Glu Leu Tyr Arg Asn Tyr Gly Ile Leu Ala Asp
 1               5                  10                  15

Ala Thr Glu Gln Val Gly Gln His Lys Asp Ala Tyr Gln Val Ile Leu
            20                  25                  30

Asp Gly Val Lys Gly Gly Thr Lys Glu Lys Arg Leu Ala Ala Gln Phe
            35                  40                  45

Ile Pro Lys Phe Phe Lys His Phe Pro Glu Leu Ala Asp Ser Ala Ile
        50                  55                  60

Asn Ala Gln Leu Asp Leu Cys Glu Asp Glu Asp Val Ser Ile Arg Arg
65                  70                  75                  80

Gln Ala Ile Lys Glu Leu Pro Gln Phe Ala Thr Gly Glu Asn Leu Pro
            85                  90                  95

Arg Val Ala Asp Ile Leu Thr Gln Leu Leu Gln Thr Asp Asp Ser Ala
            100                 105                 110

Glu Phe Asn Leu Val Asn Asn Ala Leu Leu Ser Ile Phe Lys Met Asp
            115                 120                 125

Ala Lys Gly Thr Leu Gly Gly Leu Phe Ser Gln Ile Leu Gln Gly Glu
            130                 135                 140

Asp Ile Val Arg Glu Arg Ala Ile Lys Phe Leu Ser Thr Lys Leu Lys
145                 150                 155                 160

Thr Leu Pro Asp Glu Val Leu Thr Lys Glu Val Glu Glu Leu Ile Leu
```

```
                        165                 170                 175
Thr Glu Ser Lys Lys Val Leu Glu Asp Val Thr Gly Glu Glu Phe Val
                180                 185                 190
Leu Phe Met Lys Ile Leu Ser Gly Leu Lys Ser Leu Gln Thr Val Ser
            195                 200                 205
Gly Arg Gln Gln Leu Val Glu Leu Val Ala Glu Gln Ala Asp Leu Glu
        210                 215                 220
Gln Thr Phe Asn Pro Ser Asp Pro Asp Cys Val Asp Arg Leu Leu Gln
225                 230                 235                 240
Cys Thr Arg Gln Ala Val Pro Leu Phe Ser Lys Asn Val His Ser Thr
                245                 250                 255
Arg Phe Val Thr Tyr Phe Cys Glu Gln Val Leu Pro Asn Leu Gly Thr
            260                 265                 270
Leu Thr Thr Pro Val Glu Gly Leu Asp Ile Gln Leu Glu Val Leu Asn
        275                 280                 285
Leu Leu Ala Glu Met Ser Ser Phe Cys Gly Asp Met Glu Lys Leu Glu
    290                 295                 300
Thr Asn Leu Arg Lys Leu Phe Asp Lys Leu Leu Glu Tyr Met Pro Leu
305                 310                 315                 320
Pro Pro Glu Glu Ala Glu Asn Gly Glu Asn Ala Gly Asn Glu Glu Pro
                325                 330                 335
Lys Leu Gln Phe Ser Tyr Val Glu Cys Leu Leu Tyr Ser Phe His Gln
            340                 345                 350
Leu Gly Arg Lys Leu Pro Asp Phe Leu Thr Ala Lys Leu Asn Ala Glu
        355                 360                 365
Lys Leu His Glu Ser Lys Ile Arg Leu Gln Tyr Phe Ala Arg Gly Leu
    370                 375                 380
Gln Val Tyr Ile Arg Gln Leu Arg Leu Ala Leu Gln Gly Lys Thr Gly
385                 390                 395                 400
Glu Ala Leu Lys Thr Glu Glu Asn Lys Ile Lys Val Val Ala Leu Lys
                405                 410                 415
Ile Thr Asn Asn Ile Asn Val Leu Ile Lys Asp Leu Phe His Ile Pro
            420                 425                 430
Pro Ser Tyr Lys Ser Thr Val Thr Leu Ser Trp Lys Pro Val Gln Lys
        435                 440                 445
Val Glu Ile Gly Gln Lys Arg Ala Ser Glu Asp Thr Thr Ser Gly Ser
    450                 455                 460
Pro Pro Lys Lys Ser Ser Ala Gly Pro Lys Arg Asp Ala Arg Gln Ile
465                 470                 475                 480
Tyr Asn Leu Pro Ser Gly Lys Tyr Ser Ser Asn Leu Ser Asn Phe Asn
                485                 490                 495
Tyr Glu Arg Ser Leu Gln Gly Lys
            500
```

<210> SEQ ID NO 5
<211> LENGTH: 1010
<212> TYPE: DNA
<213> ORGANISM: Mus musculus

<400> SEQUENCE: 5
acaagatttg tgacgtatttt ctgtgagcaa gttctcccta acctcagcac cctgaccacc      60
ccagtggaag gcctcgatat acagctggag gtattaaatt tgttggcaga gatgagttca     120
ttttgtggtg acatggaaaa actagaaaca aatttaagaa aactgtttga taagttattg     180

```
gagtatatgc ctctccctcc agaagaagca gaaaatgggg agaatgctgg taatgaggag    240
cccaagctgc agttcagtta tgtggagtgc ttattgtaca gttttcatca gttggggcga    300
aaacttccag acttcttaac agccaaactg aatgcagaaa aactcaagga tttcaaaatt    360
aggttgcagt actttgcacg gggcctgcag gtttatatca gacaacttcg cttggctctc    420
cagggtaaaa caggcgaggc cttaaaaaca gaggagaaca agataaaagt tgttgcactg    480
aaaataacaa acaatatcaa tgttttaatc aaggatctct tccacattcc tccttcttat    540
aagagcacac taacattgtc ctggaaacct gtgcagaaag ttgagattgg caaaagaga    600 accagtgaag atacaagttc aggttcacca cctaagaagt ctccaggagg accaaaaga    660 gatgccagac agatttataa tcctccgagt ggaaagtaca gcagcaatct gagcaacttt    720
aattatgaga ggagccttca ggggaaatag aggtggccga ggttgggaa cacgaggaaa    780 tcgaagtcga ggaagactct actgattgtg acgtcacatt cttcagcatt gtcatgagat    840
taatatactt aaatctacta ctcattggat tgccgggat gtcccttta aaggactgct    900 gccttcagct gaaaatgtaa tgttctttct acctttgtat gtatgatcta cttttgtaaa    960
agaccatggt tgtgtccaag gtaaaaccac aacaatattt ttggatgctt              1010
```

<210> SEQ ID NO 6
<211> LENGTH: 212
<212> TYPE: PRT
<213> ORGANISM: Mus musculus

<400> SEQUENCE: 6

```
Met Ser Ser Phe Cys Gly Asp Met Glu Lys Leu Glu Thr Asn Leu Arg
  1               5                  10                  15

Lys Leu Phe Asp Lys Leu Leu Glu Tyr Met Pro Leu Pro Pro Glu Glu
                 20                  25                  30

Ala Glu Asn Gly Glu Asn Ala Gly Asn Glu Glu Pro Lys Leu Gln Phe
             35                  40                  45

Ser Tyr Val Glu Cys Leu Leu Tyr Ser Phe His Gln Leu Gly Arg Lys
         50                  55                  60

Leu Pro Asp Phe Leu Thr Ala Lys Leu Asn Ala Glu Lys Leu Lys Asp
 65                  70                  75                  80

Phe Lys Ile Arg Leu Gln Tyr Phe Ala Arg Gly Leu Gln Val Tyr Ile
                 85                  90                  95

Arg Gln Leu Arg Leu Ala Leu Gln Gly Lys Thr Gly Glu Ala Leu Lys
            100                 105                 110

Thr Glu Glu Asn Lys Ile Lys Val Val Ala Leu Lys Ile Thr Asn Asn
            115                 120                 125

Ile Asn Val Leu Ile Lys Asp Leu Phe His Ile Pro Pro Ser Tyr Lys
        130                 135                 140

Ser Thr Val Thr Leu Ser Trp Lys Pro Val Gln Lys Val Glu Ile Gly
145                 150                 155                 160

Gln Lys Arg Thr Ser Glu Asp Thr Ser Ser Gly Ser Pro Lys Lys
                165                 170                 175

Ser Pro Gly Gly Pro Lys Arg Asp Ala Arg Gln Ile Tyr Asn Pro Pro
            180                 185                 190

Ser Gly Lys Tyr Ser Ser Asn Leu Ser Asn Phe Asn Tyr Glu Arg Ser
        195                 200                 205

Leu Gln Gly Lys
    210
```

<210> SEQ ID NO 7
<211> LENGTH: 205
<212> TYPE: PRT
<213> ORGANISM: Mus musculus

<400> SEQUENCE: 7

Met Glu Lys Leu Glu Thr Asn Leu Arg Lys Leu Phe Asp Lys Leu Leu
1               5                   10                  15

Glu Tyr Met Pro Leu Pro Glu Glu Ala Glu Asn Gly Glu Asn Ala
            20                  25                  30

Gly Asn Glu Glu Pro Lys Leu Gln Phe Ser Tyr Val Glu Cys Leu Leu
        35                  40                  45

Tyr Ser Phe His Gln Leu Gly Arg Lys Leu Pro Asp Phe Leu Thr Ala
50                  55                  60

Lys Leu Asn Ala Glu Lys Leu Lys Asp Phe Lys Ile Arg Leu Gln Tyr
65                  70                  75                  80

Phe Ala Arg Gly Leu Gln Val Tyr Ile Arg Gln Leu Arg Leu Ala Leu
                85                  90                  95

Gln Gly Lys Thr Gly Glu Ala Leu Lys Thr Glu Glu Asn Lys Ile Lys
            100                 105                 110

Val Val Ala Leu Lys Ile Thr Asn Asn Ile Asn Val Leu Ile Lys Asp
        115                 120                 125

Leu Phe His Ile Pro Pro Ser Tyr Lys Ser Thr Val Thr Leu Ser Trp
130                 135                 140

Lys Pro Val Gln Lys Val Glu Ile Gly Gln Lys Arg Thr Ser Glu Asp
145                 150                 155                 160

Thr Ser Ser Gly Ser Pro Pro Lys Lys Ser Pro Gly Gly Pro Lys Arg
                165                 170                 175

Asp Ala Arg Gln Ile Tyr Asn Pro Pro Ser Gly Lys Tyr Ser Ser Asn
            180                 185                 190

Leu Ser Asn Phe Asn Tyr Glu Arg Ser Leu Gln Gly Lys
        195                 200                 205

<210> SEQ ID NO 8
<211> LENGTH: 212
<212> TYPE: PRT
<213> ORGANISM: Homo sapiens

<400> SEQUENCE: 8

Met Ser Ser Phe Cys Gly Asp Met Glu Lys Leu Glu Thr Asn Leu Arg
1               5                   10                  15

Lys Leu Phe Asp Lys Leu Leu Glu Tyr Met Pro Leu Pro Glu Glu
            20                  25                  30

Ala Glu Asn Gly Glu Asn Ala Gly Asn Glu Glu Pro Lys Leu Gln Phe
        35                  40                  45

Ser Tyr Val Glu Cys Leu Leu Tyr Ser Phe His Gln Leu Gly Arg Lys
50                  55                  60

Leu Pro Asp Phe Leu Thr Ala Lys Leu Asn Ala Glu Lys Leu His Glu
65                  70                  75                  80

Ser Lys Ile Arg Leu Gln Tyr Phe Ala Arg Gly Leu Gln Val Tyr Ile
                85                  90                  95

Arg Gln Leu Arg Leu Ala Leu Gln Gly Lys Thr Gly Glu Ala Leu Lys
            100                 105                 110

Thr Glu Glu Asn Lys Ile Lys Val Val Ala Leu Lys Ile Thr Asn Asn
        115                 120                 125

Ile Asn Val Leu Ile Lys Asp Leu Phe His Ile Pro Pro Ser Tyr Lys

```
            130                 135                 140
Ser Thr Val Thr Leu Ser Trp Lys Pro Val Gln Lys Val Glu Ile Gly
145                 150                 155                 160

Gln Lys Arg Ala Ser Glu Asp Thr Thr Ser Gly Ser Pro Pro Lys Lys
                165                 170                 175

Ser Ser Ala Gly Pro Lys Arg Asp Ala Arg Gln Ile Tyr Asn Leu Pro
            180                 185                 190

Ser Gly Lys Tyr Ser Ser Asn Leu Ser Asn Phe Asn Tyr Glu Arg Ser
        195                 200                 205

Leu Gln Gly Lys
    210

<210> SEQ ID NO 9
<211> LENGTH: 205
<212> TYPE: PRT
<213> ORGANISM: Homo sapiens

<400> SEQUENCE: 9

Met Glu Lys Leu Glu Thr Asn Leu Arg Lys Leu Phe Asp Lys Leu Leu
1               5                   10                  15

Glu Tyr Met Pro Leu Pro Pro Glu Glu Ala Glu Asn Gly Glu Asn Ala
            20                  25                  30

Gly Asn Glu Glu Pro Lys Leu Gln Phe Ser Tyr Val Glu Cys Leu Leu
        35                  40                  45

Tyr Ser Phe His Gln Leu Gly Arg Lys Leu Pro Asp Phe Leu Thr Ala
    50                  55                  60

Lys Leu Asn Ala Glu Lys Leu His Glu Ser Lys Ile Arg Leu Gln Tyr
65                  70                  75                  80

Phe Ala Arg Gly Leu Gln Val Tyr Ile Arg Gln Leu Arg Leu Ala Leu
                85                  90                  95

Gln Gly Lys Thr Gly Glu Ala Leu Lys Thr Glu Glu Asn Lys Ile Lys
            100                 105                 110

Val Val Ala Leu Lys Ile Thr Asn Asn Ile Asn Val Leu Ile Lys Asp
        115                 120                 125

Leu Phe His Ile Pro Pro Ser Tyr Lys Ser Thr Val Thr Leu Ser Trp
    130                 135                 140

Lys Pro Val Gln Lys Val Glu Ile Gly Gln Lys Arg Ala Ser Glu Asp
145                 150                 155                 160

Thr Thr Ser Gly Ser Pro Pro Lys Ser Ser Ala Gly Pro Lys Arg
                165                 170                 175

Asp Ala Arg Gln Ile Tyr Asn Leu Pro Ser Gly Lys Tyr Ser Ser Asn
            180                 185                 190

Leu Ser Asn Phe Asn Tyr Glu Arg Ser Leu Gln Gly Lys
        195                 200                 205

<210> SEQ ID NO 10
<211> LENGTH: 21
<212> TYPE: DNA
<213> ORGANISM: Artificial Sequence
<220> FEATURE:
<221> NAME/KEY: misc_feature
<222> LOCATION: (0)...(0)
<223> OTHER INFORMATION: PCR primer

<400> SEQUENCE: 10
ctccggatcc actagtaacg g                                           21
```

```
<210> SEQ ID NO 11
<211> LENGTH: 20
<212> TYPE: DNA
<213> ORGANISM: Artificial Sequence
<220> FEATURE:
<221> NAME/KEY: misc_feature
<222> LOCATION: (0)...(0)
<223> OTHER INFORMATION: PCR primer

<400> SEQUENCE: 11
tctagatgca tgctcgagcg                                              20

<210> SEQ ID NO 12
<211> LENGTH: 26
<212> TYPE: DNA
<213> ORGANISM: Artificial Sequence
<220> FEATURE:
<221> NAME/KEY: misc_feature
<222> LOCATION: (0)...(0)
<223> OTHER INFORMATION: PCR primer

<400> SEQUENCE: 12
gcggatccga gatgagttca tttcgt                                       26

<210> SEQ ID NO 13
<211> LENGTH: 28
<212> TYPE: DNA
<213> ORGANISM: Artificial Sequence
<220> FEATURE:
<221> NAME/KEY: misc_feature
<222> LOCATION: (0)...(0)
<223> OTHER INFORMATION: PCR primer

<400> SEQUENCE: 13
ttgtctgata taaacctgca ggcccctg                                     28

<210> SEQ ID NO 14
<211> LENGTH: 23
<212> TYPE: DNA
<213> ORGANISM: Artificial Sequence
<220> FEATURE:
<221> NAME/KEY: misc_feature
<222> LOCATION: (0)...(0)
<223> OTHER INFORMATION: PCR primer

<400> SEQUENCE: 14
gcggatccct atttcccctg aag                                          23

<210> SEQ ID NO 15
<211> LENGTH: 32
<212> TYPE: DNA
<213> ORGANISM: Artificial Sequence
<220> FEATURE:
<221> NAME/KEY: misc_feature
<222> LOCATION: (0)...(0)
<223> OTHER INFORMATION: PCR primer

<400> SEQUENCE: 15
caggtttata tcagacaact tcgcttggct ct                                32

<210> SEQ ID NO 16
<211> LENGTH: 15
<212> TYPE: DNA
<213> ORGANISM: Artificial Sequence
<220> FEATURE:
<221> NAME/KEY: misc_feature
<222> LOCATION: (0)...(0)
<223> OTHER INFORMATION: PCR primer
```

```
<400> SEQUENCE: 16
tggcgccgac gaggt                                                    15

<210> SEQ ID NO 17
<211> LENGTH: 15
<212> TYPE: DNA
<213> ORGANISM: Artificial Sequence
<220> FEATURE:
<221> NAME/KEY: misc_feature
<222> LOCATION: (0)...(0)
<223> OTHER INFORMATION: PCR primer

<400> SEQUENCE: 17
agcattgttc accag                                                    15

<210> SEQ ID NO 18
<211> LENGTH: 15
<212> TYPE: PRT
<213> ORGANISM: Artificial Sequence
<220> FEATURE:
<223> OTHER INFORMATION: Synthetic antigen

<400> SEQUENCE: 18

Cys Asn Leu Ser Asn Phe Asn Tyr Glu Arg Ser Leu Gln Gly Lys
 1               5                  10                  15
```